(12) United States Patent
Wikswo et al.

(10) Patent No.: US 7,534,601 B2
(45) Date of Patent: May 19, 2009

(54) CAPILLARY PERFUSED BIOREACTORS WITH MULTIPLE CHAMBERS

(75) Inventors: John P. Wikswo, Brentwood, TN (US); Franz J. Baudenbacher, Franklin, TN (US); Alex Prokop, Nashville, TN (US); Eugene J. Leboeuf, Franklin, TN (US); Chang Y. Chung, Franklin, TN (US); David Cliffel, Nashville, TN (US); Frederick R. Haselton, Nashville, TN (US); William H. Hofmeister, Nashville, TN (US); Charles P. Lin, Brentwood, TN (US); Lisa J. McCawley, Nashville, TN (US); Randall S. Reiserer, Nashville, TN (US); Mark A. Stremler, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 155 days.

(21) Appl. No.: 10/525,559

(22) PCT Filed: Aug. 27, 2003

(86) PCT No.: PCT/US03/26801

§ 371 (c)(1),
(2), (4) Date: Oct. 24, 2005

(87) PCT Pub. No.: WO2004/020342

PCT Pub. Date: Mar. 11, 2004

(65) Prior Publication Data

US 2006/0141607 A1    Jun. 29, 2006

Related U.S. Application Data

(60) Provisional application No. 60/406,278, filed on Aug. 27, 2002.

(51) Int. Cl.
*C12M 1/00*   (2006.01)
(52) U.S. Cl. .................................. 435/289.1
(58) Field of Classification Search .............. 435/289.1, 435/4, 7.92, 287.1–287.5, 7.2; 436/514; 422/249, 246
See application file for complete search history.

(56) References Cited

U.S. PATENT DOCUMENTS

| 4,201,845 | A | * | 5/1980 | Feder et al. ............... 435/297.2 |
| 4,391,151 | A | * | 7/1983 | Nelson et al. ............. 73/863.23 |
| 4,988,623 | A | | 1/1991 | Schwarz et al. |
| 5,376,548 | A | * | 12/1994 | Matsuo et al. ............ 435/297.2 |
| 5,443,985 | A | | 8/1995 | Lu et al. |
| 5,489,515 | A | | 2/1996 | Hatschek et al. |
| 5,635,358 | A | | 6/1997 | Wilding et al. |
| 5,955,029 | A | | 9/1999 | Wilding et al. |
| 6,124,138 | A | | 9/2000 | Woudenberg et al. |
| 6,168,948 | B1 | | 1/2001 | Anderson et al. |
| 6,171,239 | B1 | | 1/2001 | Humphrey |
| 6,267,858 | B1 | | 7/2001 | Parce et al. |
| 6,440,645 | B1 | | 8/2002 | Yon-Hin et al. |
| 6,506,345 | B1 | * | 1/2003 | Lee et al. ................. 422/100 |
| 2002/0058329 | A1 | | 5/2002 | Singh et al. |
| 2002/0106786 | A1 | | 8/2002 | Carcalho et al. |

FOREIGN PATENT DOCUMENTS

WO    WO 01/07892 A1    2/2001

OTHER PUBLICATIONS

Jain et al.; "In Vitro and In Vivo Quantificatiaon of Adhesion Between Leukocytes and Vascular Endothelium," Tissue engineering methods and protocols, Morgan, J.R. and Yarmush, M. L.,, eds. Humana Press, Totowa, N. J., 553-575, 1999.

Jain, R. K., "Angiogenesis and Lymphangiogensis in Tumors: Insights from Intravital Microscopy," Cold Spring Harb. Symp. Quant. Biol., 67, 239-248, 2002.

Murdin et al., "Immobilisation and Growth of Hybridomas in Packed Beds," Bioreactors and Biotransformations, Moody, G. W. and Baker, P. B., eds. Elsevier Applied Science Publishers, London, New York, 99-110, 1987.

(Continued)

*Primary Examiner*—Ann Y Lam
(74) *Attorney, Agent, or Firm*—Morris Manning Martin LLP; Tim Tingkang Xia

(57) ABSTRACT

A bioreactor for cultivating living cells in a liquid medium. In one embodiment of the present invention, the bioreactor includes a first substrate having a first surface, an opposite second surface and edges. The bioreactor further includes a second substrate having a first surface and an opposite second surface, defining a cavity with a bottom surface, where the bottom surface is located therebetween the first surface and the second surface. The first surface of the first substrate is received by the second surface of the second substrate to cover the cavity so as to form a channel for receiving cells and a liquid medium. In forming the bioreactor, the channel is sized to allow the growth of a layer of cells on a biocompatible coating layer and a flow of liquid in the channel. The flow of liquid is controlled so as to provide a known shear force to the layer of cells. The flow of liquid can be further controlled so as to provide an environment that simulates a vascular space in the channel.

14 Claims, 14 Drawing Sheets

OTHER PUBLICATIONS

Allen et al, "*Improving the Next Generation of Bioartificial Liver Devices*," Seminars in Cell & Developmental Biology, 13, 447-454, 2002.

Augenstein et al., "*Effect of Shear on Death of Two Strains of Mammalian Tissue Cells*," Biotechnol. Bioeng., 13, 409-418, 1971.

Beeton et al., "*A Novel Membrane Bioreactor for Microbial-Growth*," Appl. Microbiol. Biotechnol., 40, 812-817, 1994.

Bhujwalla et al., "*Combined Vascular and Extracellular PH Imaging of Solid Tumors*," NMR Biomed., 15,114-119, 2002.

Black et al., "*Diblock Copolymers: Self-Assembly for Applications in Microelectronics*," Encyclopedia of Materials : Science and Technology, Buschow, KHJ, ed. Elsevier, New York, 1-6, 2002.

Black et al., "*Tuominen, M. T., Integration of Self-Assembled Diblock Copolymers for Semiconductor Capacitor Fabrication*," Appl. Phys. Lett., 79, 409-411, 2001.

Borenstein et al., "*Microfabrication Technology for Vascularized Tissue Engineering, Biomedical Microdevices*," 4, 167-175, 2002.

Boyden, S., "*The Chemotactic Effect of Mixtures of Antibody and Antigen on Polymorphonuclear Leucocytes*," J. Exp. Med., 115, 453-466, 1962.

Brown et al., "*Improvements to Parallel Plate Flow Chambers to Reduce Reagent and Cellular Requirements*," BMC Immunology, 2, 9-16, 2001.

Cinamon et al., "*A Real Time in Vitro Assay for Studying Leukocyte Transendothelial Migration Under Physiological Flow Conditions*," J. Immunol. Methods, 273, 53-62, 2003.

De Bartolo et al., "*A Novel Full-Scale Flat Membrane Bioreactor Utilizing Porcine Hepatocytes: Cell Viability and Tissue-Specific Functions*," Biotechnol. Prog., 16,102-108, 2000.

Ding et al., "*Chemokines Stimulate Human T Lymphocyte Transendothelial Migration to Utilize VLA-4 in Addition to LFA-1,*" J. Leukoc. Biol., 69, 458-466, 2001.

Drioli et al., "*Biocatalytic Membrane Reactors, Applications in Biotechnology and the Pharmaceutical Industry*," Taylor & Francis, London, Philadelphia, 1999.

Dupin et al., "*Impact of Colony Morphologies and Disinfection on Biological Clogging in Porous Media*," Environ. Sci. Technol., 34, 1513-1520, 2000.

Dupin et al., "*Mesoscale and Microscale Observations of Biological Growth in a Silicon Pore Imaging Element*," Environ. Sci. Technol., 33, 1230-1236, 1999.

Falk et al., "*A 48-Well Micro Chemotaxis Assembly for Rapid and Accurate Measurement of Leukocyte Migration*," J. Immunol. Methods, 33, 239-247, 1980.

Fink et al., "*Chronic Stretch of Engineered Heart Tissue Induces Hypertrophy and Functional Improvement*," FASEB J., 14, 669-679, 2000.

Folkman et al., "*Tumor Angiogenesis-Therapeutic Implications*," N. Engl. J. Med., 285, 1182-1186, 1971.

Gillies et al., "*MRI of the Tumor Microenvironment*," J. Magn. Reson. Imaging, 16, 430-450, 2002.

Godbey et al., "*In Vitro Systems for Tissue Engineering*", Ann. N. Y., Acad. Sci., 961,10-26, 2002.

Griffith et al., "*Tissue Engineering-Current Challenges and Expanding Opportunities*," Science, 295, 1009-1014, 2002.

Griffith, L. G., "*Emerging Design Principles in Biomaterials and Scaffolds for Tissue Engineering*," Reparative Medicine: Growing Tissues and Organs, 961, 83-95, 2002.

Guarini et al., "*Nanoscale Patterning Using Self-Assembled Polymers for Semiconductor Applications*," J. Vac. Sci. & Tech. B, 19,2784-2788, 2001.

Guarini et al., "*Optimization of Diblock Copolymer Thin Film Self Assembly*," Advanced Materials, 14,1290-1294, 2002.

Guarini et al., "*Process Integration of Self-Assembled Polymer Templates into Silicon Nanofabrication*," Journal of Vacuum Science & Technology B, 20, 2788-2792, 2002.

Hammer et al., "*Measuring Receptor-Mediated Cell Adhesion Under Flow: Cell-Free Systems*," Tissue engineering methods and protocols, Morgan, J. R. and Yarmush, M. L., eds. Humana Press, Totowa, N. J., 543-552, 1999.

Heidemann et al., "*Angiogenic Effects of Interleukin 8 (CXCL8) in Human Intestinal Microvascular Endothelial Cells Are Mediated by CXCR2*," J. Biol. Chem., 278, 8508-8515, 2003.

Helmlinger, "*Acid Production in Glycolysis-Impaired Tumors Provides New Insights into Tumor Metabolism*," Clin. Cancer Res., 8, 1284-1291, 2002.

Higgs et al., "*Regulation of Actin Filament Network Formation Through Arp2/3 Complex: Activation by a Diverse Array of Proteins*," Annu. Rev. Biochem., 70, 649-676, 2001.

Hu et al., "*Large-Scale Mammalian Cell Culture*," Curr. Opin. Biotechnol., 8, 148-153, 1997.

Jackman et al., "*Electrochemistry and Soft Lithography: A Route to 3-D*," Chemtech, 29,18-30, 1999.

Jain et al., "*Dissecting Tumour Pathophysiology Using Intravital Microscopy*," Nature Reviews Cancer, 2, 266-276, 2002.

Jones et al., "*P-Selectin Mediates Neutrophil Rolling on Histamine-Stimulated Endothelial Cells*," Biophys. J., 65, 1560-1569, 1993.

Kaihara et al., "*Silicon Micromachining to Tissue Engineer Branched Vascular Channels for Liver Fabrication*," Tissue Eng., 6, 105-117, 2000.

Klemke et al., "*CAS/Crk Coupling Serves As a "Molecular Switch" for Induction of Cell Migration*," Journal of Cell Biology, 140, 961-972, 1998.

Labecki et al., "*Protein Transport in Ultrafiltration Hollow-Fiber Bioreactors for Mammalian Cell Culture*," Membrane Separations in Biotechnology, Wang, W. K., ed., M. Dekker, New York, 1-62, 2001.

Ley, K., "*The Selectins As Rolling Receptors*," The selectins: initiators of leukocyte endothelial adhesion, Vestweber, D, ed. Harwood Academic Publishers, Australia, 63-104, 1997.

Li et al., "*Cortactin Potentiates Bone Metastasis of Breast Cancer Cells*," Cancer Res, 61, 6906-11, 2001.

Li et al., "*Hexagonal Pore Arrays With a 50-420 Nm Interpore Distance Formed by Self-Organization in Anodic Alumina*," J. Appl. Phys., 84, 6023-6026, 1998.

Li et al., "*Initial Stages of Tumor Cell-Induced Angiogenesis: Evaluation Via Skin Window Chambers in Rodent Models*," J Natl Cancer Inst, 92, 143-7, 2000.

Li et al., "*On the Growth of Highly Ordered Pores in Anodized Aluminum Oxide*," Chem. Mater., 10, 2470-2480, 1998.

Lin et al., "*Antiangiogenic Gene Therapy Targeting the Endothelium-Specific Receptor Tyrosine Kinase Tie2*," Proc. Natl Acad Sci U S A, 95, 8829-34, 1998.

Lin et al., "*Inhibition of Tumor Angiogenesis Using a Soluble Receptor Establishes a Role for Tie2*," in Pathologic Vascular Growth, J Clin Invest, 100, 2072-8, 1997.

Lin et al., "*Inhibition of Tumor Growth by Targeting Tumor Endothelium Using a Soluble Vascular Endothelial Growth Factor Receptor*," Cell Growth Differ, 9, 49-58, 1998.

MacNeill et al., "*Toward a New Blood Vessel*,"Vasc. Med., 7, 41-246, 2002.

Mansky et al., "*Controlling Polymer-Surface Interactions With Random Copolymer Brushes*," Science, 275,1458-1460, 1997.

Martinez et al., "*Acidic PH Enhances the Invasive Behavior of Human Melanoma Cells, Clinical & Experimental Metastasis*," 14, 176-186, 1996.

McDonald et al., "*Poly (Dimethylsiloxane) As a Material for Fabricating Microfluidic Devices*," Accounts of Chemical Research, 35,491-499, 2002.

McDuffie N. G., Cell Culture Bioreactors. In : Bioreactor Design Fundamentals, Butterworth-Heinemann, Boston, 93-119,1991.

Millward et al., "*The Vortex Wave Membrane Bioreactor: Hydrodynamics and Mass Transfer*," Chemical Engineering Journal and the Biochemical Engineering Journal, 62, 175-181, 1996.

Mooney et al., "*Stabilized Polyglycolic Acid Fibre Based Tubes for Tissue Engineering*," Biomaterials, 17, 115-124, 1996.

Munn et al., "*Analysis of Cell Flux in the Parallel-Plate Flow Chamber-Implications for Cell Capture Studies*," Biophys. J., 67, 889-895, 1994.

Nollert et al., "*Hydrodynamic Shear-Stress and Mass-Transport Modulation of Endothelial-Cell Metabolism*," Biotechnol. Bioeng., 38, 588-602, 1991.

Papadaki et al., "*Quantitative Measurement of Shear-Stress Effects on Endothelial Cells*," Tissue engineering methods and protocols, Morgan, J. R. and Yarmush, M. L, eds. Humana Press, Totowa, N. J., 577-593, 1999.

Park et al., "*Integration of Cell Culture and Microfabrication Technology*," Biotechnol. Prog., 19, 243-253, 2003.

Passeraub et al., "*Design, Microfabrication and Analysis of a Microfluidic Chamber for the Perfusion of Brain Tissue Slices*," Biomedical Microdevices, 5, 147-155, 2003.

Powers et al., "*A Microfabricated Array Bioreactor for Perfused 3D Liver Culture*," Biotechnol. Bioeng., 78, 257-269, 2002.

Ramos et al., "*Quantitative Measurement of Cell-Cell Adhesion Under Flow Conditions*," Tissue engineering methods and protocols, Morgan, J. R. and Yarmush, M. L., eds. Humana Press, Totowa, N. J., 507-519, 1999.

Renard et al., "*Induced Changes of Leukocyte Slow Rolling in an in Flow Pharmacological Model of Adhesion to Endothelial Cells*," Biorheology, 40,173-178, 2003.

Roth et al., "*Characterization of Transendothelial Chemotaxis of T Lymphocytes*," J. Immunol. Methods, 188, 97-116, 1995.

Schultz, "*Roles of Solute and Heat-Flow in the Development of Polymer Microstructure*," Polymer, 32,3268-3283, 1991.

Snyder et al., "*Fabrication of Multiple Microscale Features on Polymer Surfaces for Applications in Tissue Engineering*." Biomedical Microdevices, 3, 293-300, 2001.

Solan et al., "*Engineered Vessels: Importance of the Extracellular Matrix*," Transplant. Proc., 33, 66-68, 2001.

Tobert et al., "*Perfusion Culture Systems for Production of Mammalian Cell Biomolecules*," Large-Scale Mammalian cell culture, Feder, J. and Tolbert, W. R., eds., Academic Press, Orlando, 97-123, 1985.

Voisard et al., "*Potential of Cell Retention Techniques for Large-Scale High-Density Perfusion Culture of Suspended Mammalian Cells*," Biotechnol. Bioeng., 82,751-765, 2003.

Walheim et al., "*Structure Formation Via Polymer Demixing in Spin-Cast Films*," Macromolecules, 30, 4995-5003,1997.

Weidner et al., "*Tumor Angiogenesis and Metastasis-Correlation in Invasive Breast-Carcinoma*," N. Engl. J. Med., 324, 1-8, 1991.

Whitesides et al., Ingber, D. E., "*Soft Lithography in Biology and Biochemistry*," Annual Review of Biomedical Engineering, 3,335-373, 2001.

Wu et al. "*Fabrication of Complex Three-Dimensional Microchannel Systems in PDMS*," J. Am. Chem. Soc., 125, 554-559, 2003.

Xia et al., "*Soft Lithography*," Annual Review of Materials Science, 28,153-184, 1998.

Yao et al., "*Chemotaxis by A Cns Macrophage*," the Microglia, J. Neurosci. Res., 27, 36-42, 1990.

Harvath, L. et al, "Rapid quantitation of neutrophil chemotaxis; use of a polyvinylpyrrolidone-free polycarbonate membrane in multiwell assembly," *J. Immunol Method*, vol. 37, No. 1, 1980, pp. 39-45.

* cited by examiner

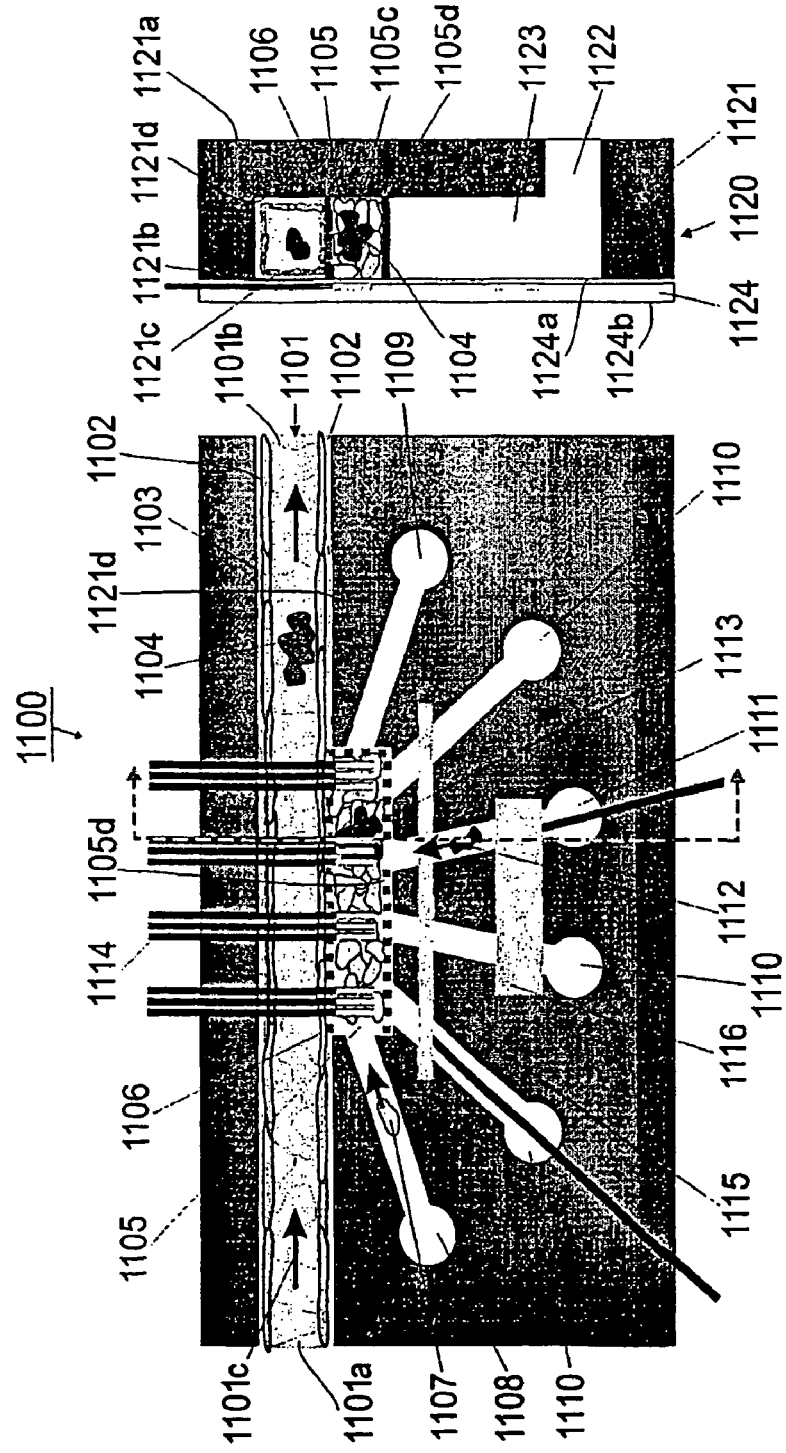
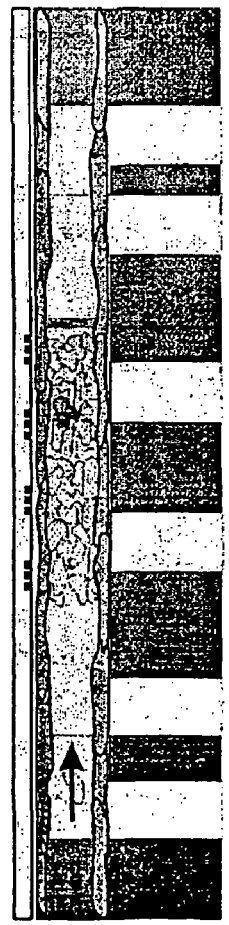
Fig. 1A1
Fig. 1A2
Fig. 1A3

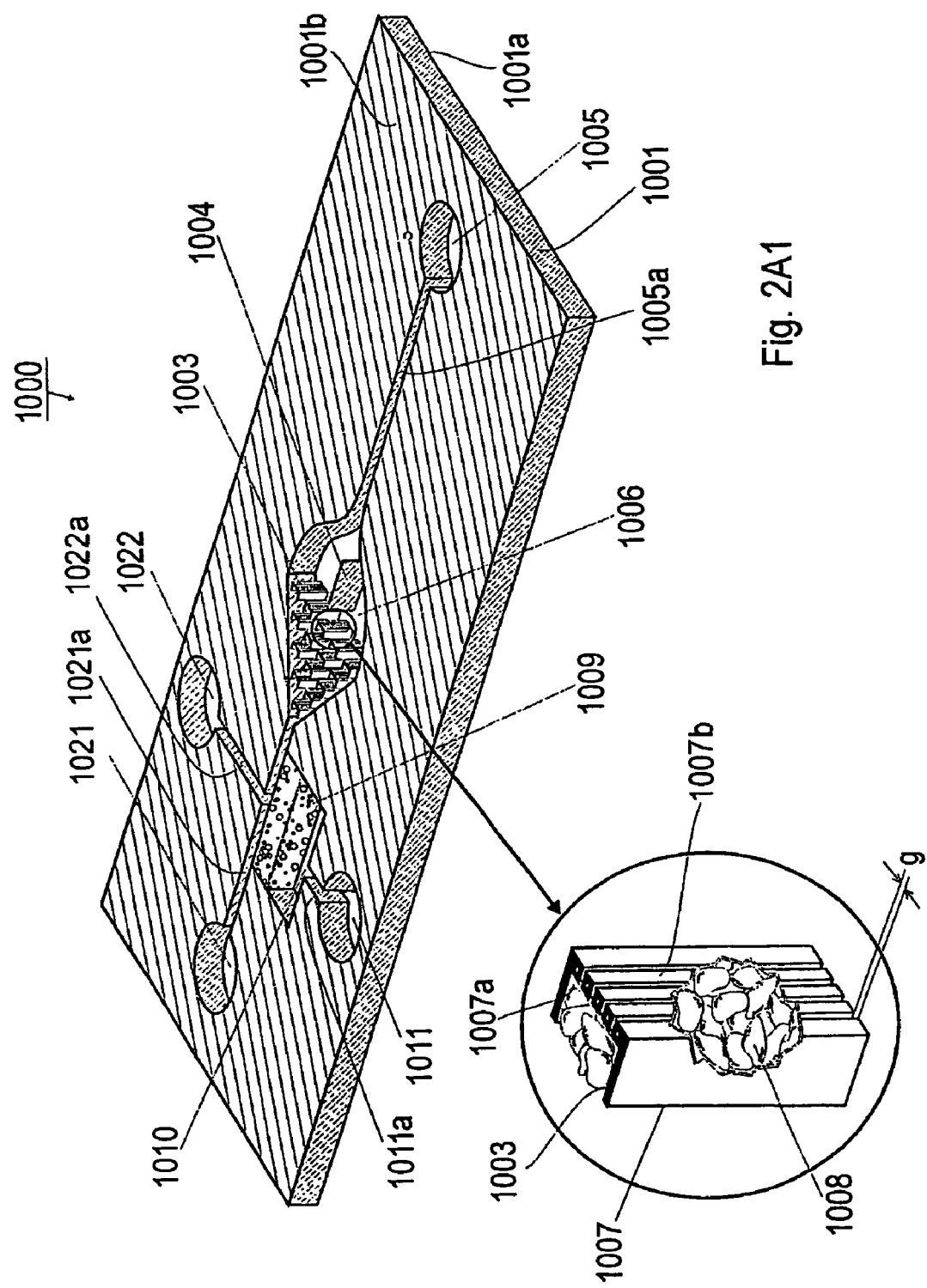
Fig. 2A1
Fig. 2A2

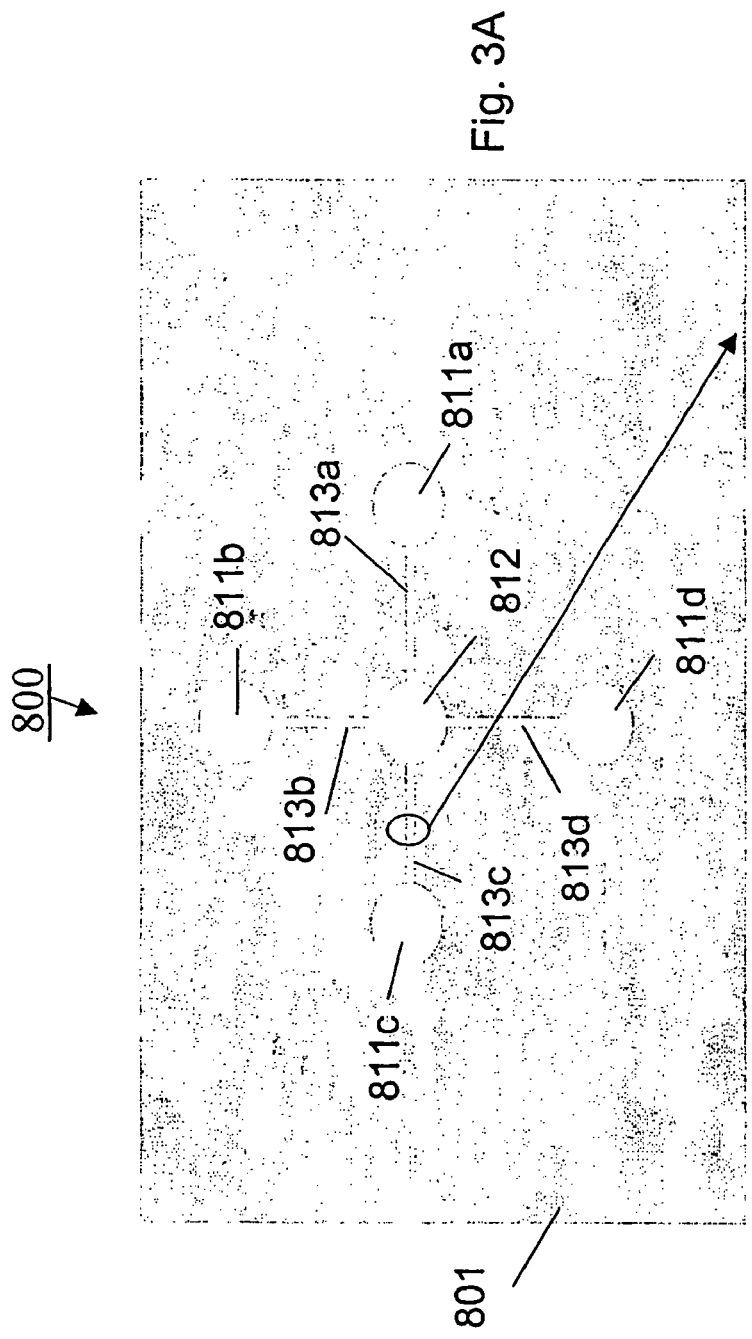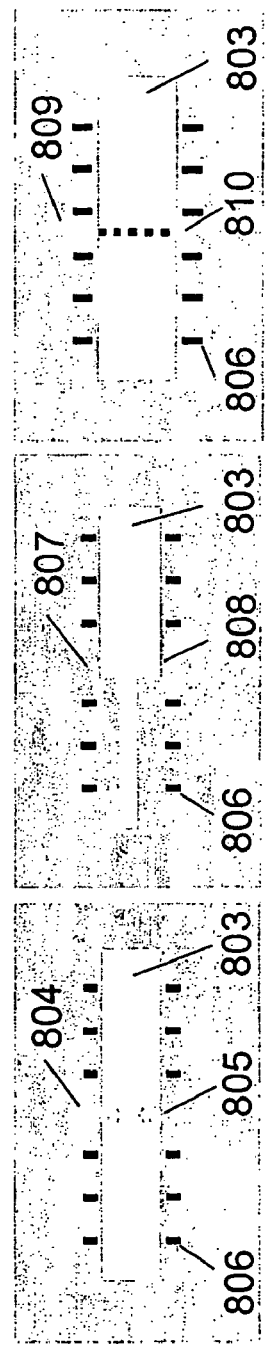
Fig. 3A
Fig. 3B
Fig. 3C
Fig. 3D

CAPILLARY PERFUSED BIOREACTORS WITH MULTIPLE CHAMBERS

The present invention was made with Government support under Grant No. N66001-01-C-8064 awarded by the Defense Advanced Research Projects Administration and the Office of Naval Research. The present invention was also made with Government support under Grant 5R43 RR016124-02 awarded by the National Institute of Health. The United States Government may have certain rights to this invention pursuant to these grants.

This application is being filed as a PCT International Patent Application in the name of Vanderbilt University, a U.S. national corporation, applicant for the designation of all countries except the US, and John P. Wikswo, Franz J. Baudenbacher, Ales Prokop, and Eugene LeBoeuf, all U.S. nationals and residents, applicants for the designation of the US only, on 27 Aug. 2003.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. In terms of notation, hereinafter, "[n]" represents the nth reference cited in the reference list. For example, [11] represents the 11th reference cited in the reference list, namely, Hu, W. S. and Aunins, J. G., Large-Scale Mammalian Cell Culture, Curr. Opin. Biotechnol., 8, 148-153, 1997.

FIELD OF THE INVENTION

The present invention generally relates to an apparatus and methods for growing and maintaining a living system. More particularly, the present invention relates to an apparatus and methods that have a channel configuration allowing perfusate flow with diffusional exchange to tissue cells but no cell migration. Additionally, the present invention relates to an apparatus and methods that have capacity for growing and maintaining a living microorganism such as protozoa.

The present invention also relates to an apparatus and methods for dynamic analysis of a collection of cells such as a biofilm. More particularly, the present invention relates to an apparatus and methods for measuring response of a biofilm to one or more dynamic streams of substance such as chemical stressors at various depths of the biofilm.

Certain embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with multiple chambers and methods of using the same.

Certain other embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with an array of chambers with a common feed line and methods of using the same.

Certain additional embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise capillary perfused bioreactors and methods of using the same.

Certain further embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with substance injection capability and methods of using the same.

BACKGROUND OF THE INVENTION

Bioreactor is a device that can be used for culturing living cells. More particularly, bioreactors are vessels that provide a proper physical and chemical environment as well as fast transport of substrates and products to allow cellular biological reactions to occur, ideally rapidly and efficiently. The simplest bioreactor is a culture dish: In conventional cell culture using well-plates, culture-dishes, and flasks, the volume of the culture medium is typically 200 to 1000 times the volume of the cells. This ratio, when used in combination with buffering of the culture media, allows the cells to grow for at least 24 hours without media change. However, another consequence of this ratio is a corresponding dilution of whatever extracellular factors are produced by the cells and might otherwise provide paracrine cell-to-cell communication, which is possible in tissue because the extracellular volume might be only 10% of intracellular volume.

Much of the development of bioreactors was directed towards either the functional tissues, or the generation of biochemicals and pharmaceuticals. For example, over the last 20 years studies on the generation of skin, pancreas, cartilage, liver, cornea and bladder have taken particular importance[1]. In the United States alone, there are more than 80,000 individuals waiting for an organ transplant, and hence the need to develop improved bioreactor technology is self-evident. There is also a growing recognition that progress in understanding cell motility and chemotactic signaling, as well as other complex cellular processes, is often constrained by the laboratory techniques available for observing and intervening at various points in the processes. Many of these processes can be examined best in a properly instrumented bioreactor.

There is a wide variety in bioreactors, including stirred vessels, bubble column, packed beds[2], air-lift reactors, and membrane reactors[3] that include plates, rotating plates, spiral-wound and hollow fibres. Hollow-fiber reactors are of special importance since (depending of their structure) they may allow as much as 30,000 $m^2$ of membrane area per $m^3$ module volume[4-6]. However, given that mammalian cells are very sensitive to shear forces[7-9] (which originate mainly from agitation and aeration), it is important to reduce the forces as much as possible in the reactor where the cells will be grown[9,10]. Membranes have been used in bioreactors to increase survival of cells. For instance, it has been known that liquid-gas interface created in some models of reactors is particularly damaging for mammalian cells. That potentially lethal interface can be eliminated by the use of a hydrophobic membrane[9].

Bioreactors may be also classified by means of their mode of operation: batch, fed-batch and continuous cultivation (also called perfused cultivation). In the first or batch mode, no substrate is added, nor medium removed; in the case of the fed-batch mode there is a continuous feeding, but nothing is removed until the reactions are terminated and the reactor emptied. While these systems imply a low effort for process control, the productivity is low compared to that in perfused systems, the third mode, where a permanent inflow of substrate and outflow of medium takes place. Besides the high productivity, there is a better cell physiology control in this kind of reactors[11] and in the case of mammalian cell culture, it has been shown to provide significant advantage over static methods[12,13].

One of the limitations when developing large three-dimensional tissues is the lack of a proper vascular supply for nutrient and metabolite transport. A number of studies have analyzed the artificial vascular networks[14-18], and there have been a number of attempts to construct functional microfabricated scaffolds[3,16,19-21]. The techniques by which these networks have been produced include plasma etching, photolithography, soft lithography, microcontact printing, microfluidic patterning using microchannels, laminar flow patterning and stencil patterning[22-25]. In the case of plasma etching technologies we can consider the high aspect ratio micromachining (HARMS) as a very powerful tool since it allows to etch channels of virtually unlimited depth without increasing the width already achieved by lithography[22]. It is also possible to construct three dimensional microchannel systems in PDMS with complex topologies and geometries[15].

Additionally, one needs to realize that the growth of clinically-implantable tissue may require the ultimate biodegradation and the mechanical properties of the tissue scaffold[16]. These properties are directly related to the crystallinity, molecular weight, glass transition temperature and monomer hydrophobicity of the materials chosen to fabricate the tissue[19]. Naturally derived materials such as collagen have been employed[26], as well as synthetic and semi synthetic ones. Polyglycolic acid (PGA) possesses high porosity and it makes easy the fabrication of devices, therefore, PGA fibre meshes have been considered to transplant cells. However, they cannot resist significant compressional forces. An alternative to solve this problem is to use polymers of lactic and glycolic acid whose ratios can be adjusted to control the crystallinity of the material and hence the degradation rate and mechanical properties. Fibre-based tubes have been fabricated from these polymers[27].

It is important to compare the vascular nature of living tissue with the capabilities provided by existing microfabricated cell-perfusion bioreactor systems. In tissue, arteries divide into progressively smaller vessels, eventually reaching arterioles and then capillaries. The arterioles are important because they contain the precapillary sphincters, which allow control of the perfusion of individual capillary beds, but also provide the majority of the peripheral resistance and hence the pressure drop associated with the arterial supply. As a result, the pressure difference across the capillary endothelium membrane is kept sufficiently low to allow diffusional transport of nutrients and metabolites across the membrane, as well as the trafficking of immune cells required for tissue maintenance and infection control. Were the pressures in the capillaries as high as those in the arterioles, the capillary wall thickness would be too great to allow these critical transport phenomena. The venous return system is in many ways a mirror of the arterial system, albeit at lower pressures. Another feature of the living vascular system is that the branching process described above allows all cells to be within 50 to 200 microns of a capillary, depending upon the specific tissue. As a result, the arterial supply and venous return systems are intercalated in such a manner that every capillary that perfuses a large group of cells is connected to the larger supply and return systems with a self-similarity that ensures uniform perfusion and transcapillary pressures. It is this intercalation process that is so difficult to replicate with microfabrication. For example, Borenstein et al.,[22] describe a process to build a two-dimensional vascular system that could create a multi-scale perfusion system for supporting endothelial cells, but there is no provision to selectively limit diffusive transport across the smallest capillaries to perfuse cells lying outside of the perfusion network. More importantly, the networks they show have a large region of the device that is covered with the larger vessels, and the region of the bioreactor that is limited to capillary vessels is in fact quite small.

Thus, there is a need for microfabricated migration bioreactors that mimic in vitro the microenvironments of normal tissue was well as that of tumors, infected tissue, and wounded tissue, while providing independent control of chemokine and growth factor gradients, shear forces, cellular perfusion, and the permeability of physical barriers to cellular migration, thereby allowing detailed optical and electrochemical observation of normal, immune, and cancerous cells during cell migration, intravasation, extravasation, and angiogenesis. Angiogenesis, tumor metastasis, and leukocyte infiltration into tissue are complex processes that are regulated not only by cellular responses to a single chemokine, but also by external factors, such as multiple competing chemokine and growth factor signals, autocrine feedback loops, cell-cell interactions, and mechanical forces such as vessel shear stress. Current approaches for assessing migration across cellular barriers include Boyden and transwell chambers that provide an integrated fluorescence assay of migration across filters to allow quantitation of migration[28-34], parallel plate flow chambers[35-38], in which adhesion and rolling on endothelial cells in shear stress can be assessed[35,39-44], and in vivo intravital microscopy in which migration of cells in living animals is visualized[45-48]. Each of these approaches has limitations, including the inability to have sustained and controlled chemotactic gradients (all systems), the inability to visualize migration in real time or with physiologic shear stress (Boyden and transwell chambers), the inability to observe extravasation or angiogenesis into an underlying, deep cellular matrix (parallel plate flow chambers) and the inability to control all aspects of the experiments, e.g., having defined cell populations and controlled microfluidics for independent control of shear and tissue perfusion (all systems, especially intravital microscopy). The development of a motility/metastasis model system with independent control of endothelial shear stress, chemokine gradients, tissue perfusion, and the ability to add different cell types through different ports, combined with state-of the art imaging techniques and sensor capabilities would represent a huge advance over currently available systems.

Indeed, the need for such capabilities is quite urgent. Angiogenesis is a dynamic process, influenced by the cellular microenvironment and intricately linked to metastasis[49,50]. It has been demonstrated that both VEGF and angiopoietin/tyrosine kinase (Ang/Tie2) function are required for tumor angiogenesis[51-53]. However, how signals from those two receptor systems are integrated to mediate angiogenesis has not been determined, in part due to the lack of good model systems. The next step would be to study the coordination and integration of VEGF and Ang signaling in endothelial cell migration, vascular sprouting and maturation, and tumor transendothelium migration. As with angiogenesis, multiple environmental inputs affect tumor metastasis and leukocyte infiltration. Activation of one chemokine receptor in tumor cells affects the induction of other ligands and receptors in tumor cells as well as endothelial cells and leukocytes, but the mechanism is poorly understood[54]. There is a need for an understanding of how alteration of chemokine receptor internalization and/or changes in receptor association with adaptor molecules such as AP-2 or beta-arresting affect chemokine receptor activity as tumor cells move through a complex matrix. How external factors such as cell-cell adhesion, cell-matrix interactions, and vessel shear stress affect cytoskeletal reorganization during migration through tissues is also poorly understood. Cortactin overexpression increases the metastasis of breast cancer cells to bone[55], however the mechanism remains unclear. Likewise, lack of WASp protein in humans leads to an X-linked immune disorder that may result from signaling, proliferation or chemotaxis defects[56]. There is a need to study the role of cortactin and WASp proteins in chemotaxis of breast cancer and HL60 cells in a complex multicell environment involving controllable shear, cell-cell interactions, and chemokine gradients. As a final example, matrix metalloproteinases (MMPs) are extracellularly expressed enzymes found in many types of cancer and are thought to be important in tumor development, growth, invasion and metastasis. It has recently been discovered that skin tumors that develop in mice deficient for MMP-3 (MMP-3 null mice) progress and grow much faster than skin tumors from normal, wild-type mice. This difference is associated with a reduced number of immune cells in the tumor and surrounding tissue in the MMP-3 null mice. The logical progression of this research is to determine how loss of an MMP affects the ability of immune cells, namely monocytes and neutrophils, to infiltrate from the peripheral blood circulation to the tumor site. The ability to control the experimental environment, including multiple defined cell populations, is critical to elucidate the relative importance of tumor-host interactions in MMP-3 induced cellular chemotaxis.

Despite the progress made over the years, however, currently available bioreactors cannot provide a more physiologic environment that would include a three-dimensional in vitro region with multiple cell types, stimuli, and measurement capabilities and allows study of molecular aspects of the chemotactic response. Thus, bioreactors that mimic in vitro the microenvironments of tumors and tissue while providing independent control of chemokine and growth factor gradients, shear forces, cellular perfusion, and the permeability of physical barriers to cellular migration, thereby allowing detailed optical and electrochemical observation of normal and cancerous cells during cell migration, intravasation, extravasation, and angiogenesis need to be developed.

Therefore, a heretofore unaddressed need exists in the art to address the aforementioned deficiencies and inadequacies.

SUMMARY OF THE INVENTION

In one aspect, the present invention relates to a bioreactor for cultivating living cells in a liquid medium. In one embodiment, the bioreactor includes a first substrate having a first surface, an opposite second surface and edges. The bioreactor further includes a second substrate having a first surface and an opposite second surface, defining a cavity with a bottom surface, where the bottom surface is located therebetween the first surface and the second surface. The first surface of the first substrate is received by the second surface of the second substrate to cover the cavity so as to form a channel for receiving cells and a liquid medium. The second substrate can be fabricated from glass, Mylar, PDMS, silicon, a polymer, a semiconductor, or any combination of them. The first substrate is at least partially optically transparent such that the dynamic activities of cells in the channel are detectable through optical detecting means.

A recess is formed in the second substrate with a bottom surface and in fluid communication with the channel. Additionally, a barrier is positioned for covering the recess so as to form an outer chamber. The barrier has a porosity to allow the channel and the outer chamber to be in fluid communication and control the move of at least one predetermined type of cells between the channel and the outer chamber. In one embodiment, the barrier includes a plurality of posts spaced with a gap from each other. These posts may be coated in certain locations with substances to prevent entry of cells, particularly the endothelial cells. Gaps between the posts in certain locations allow for delivery of particular cell types to the outer chamber.

The second substrate further defines a first opening and an opposite, second opening adapted for allowing a flow of liquid to be introduced into the channel through the first opening and away from the channel through the second opening substantially along a first direction.

The bioreactor further includes a biocompatible coating layer applied to the interior surfaces of the second substrate around the channel. The biocompatible coating layer includes a material that may inhibit cell adhesion to the biocompatible coating layer, enhance cell adhesion to the biocompatible coating layer, promote organization and growth of cells, or function as a fluorescent marker or indicator of the state of cells. In forming the bioreactor, the channel is sized to allow the growth of a layer of cells on the biocompatible coating layer and the flow of liquid in the channel. The flow of liquid is controlled so as to provide a known shear force to the layer of cells. The flow of liquid can be further controlled so as to provide an environment that simulates a vascular space in the channel.

The cells can be any type of living cells, including, but not limited to, bacteria, protozoa, or both, normal cells, endothelial cells, tumor cells, or any combination of them. Cells can be introduced into the channel individually, in a collection of cells, or in the form of biofilm. In one embodiment, the layer of cells substantially forms an endothelial cell-lined capillary in the channel. The channel is sized such that when at least one cell that is not one of the endothelial cells, such as a tumor cell, is introduced into the channel, it can undergo intravasation in the endothelial cell-lined capillary.

The second substrate further defines one or more injection ports, in fluid communication with the channel to allow a stream of substance to be introduced into the channel through the injection port, substantially along a second direction, respectively. The second direction is substantially perpendicular to the first direction. The stream of substance is controlled so as to provide a gradient to the channel. The stream of substance includes a substance affecting the growth of cells such as chemokine.

The outer chamber is sized to allow the growth of a host of cells. The host of cells includes at least a first type of cells and a second type of cells that is different from the first type of cells. In other words, the outer chamber is sized to allow the growth of two types of cells. In one embodiment, the first type of cells includes normal cells, and the second type of cells includes tumor cells. A port and a connection channel are formed in the second substrate such that the connection channel is in fluid communication with the outer chamber and the port. The bioreactor further includes a plurality of electrodes adapted for electrochemical measurements of the host of cells. Moreover, the bioreactor further includes a plurality of controlling ports, and a plurality of connection channels, wherein each of the connection channels is in fluid communication with a corresponding one of controlling port, and the outer chamber, respectively.

The bioreactor can be used as a capillary perfused migration bioreactor for the study of cancer cells or neutrophil extravasation in the presence of two competing chemokine gradients. In particular, a first stream of chemokine is injected through a port and hence creates a first gradient of that chemokine both in the outer chamber and the channel. Additionally, a second stream of chemokine is injected through a port and hence creates a second gradient of that chemokine both in the outer chamber and the channel.

In another aspect, the present invention relates to another type of bioreactor and its variants for cultivating living cells in a liquid medium. In one embodiment, the bioreactor includes a first substrate having a first surface and an opposite second surface, defining a chamber therebetween for receiving cells and a liquid medium. The first substrate can be fabricated from glass, Mylar, PDMS, silicon, a polymer, a semiconductor, or any combination of them.

An inlet port and a first connection channel are formed in the first substrate, where the first connection channel is in fluid communication with the inlet port and the chamber for allowing a stream of substance to be delivered to the chamber. Additionally, an outlet port and a second connection channel are formed in the first substrate, where the second connection channel is in fluid communication with the outlet port and the chamber for allowing a stream of substance to be removed from the chamber.

Moreover, the bioreactor has confining means positioned in a region in the chamber proximate to the first connection channel to confine the cells. In one embodiment, the confining means includes a plurality of traps, where each of the plurality of traps is capable of receiving at least one cell or a collection of cells. Each of the plurality of traps includes a structure defining a recess so as to receive and confine one or more cells therein. The structure may be partially formed with a filter to allow the recess to be in fluid communication with the chamber. The filter can be formed with a plurality of posts spacing from each other with a gap g. Traps can take various shapes and have different physics properties. The plurality of traps can be arranged to form an array.

Additionally, the first substrate defines a first alternate port and a third connection channel in fluid communication with the first alternate port and the first connection channel for allowing additional substance to be introduced into the chamber. Moreover, the first substrate further defines a second alternate port, a third connection channel, and a second chamber, wherein the third connection channel is in fluid communication with second alternate port and the second chamber, and the second chamber is in fluid communication with the first connection channel. Furthermore, the second chamber is formed with an oxygen permeable structure to provide oxygen to the cells.

The bioreactor further includes a second substrate having a first surface and an opposite, second surface, and means adapted for electrochemical measurements of the cells in the chamber. The means for electrochemical measurements is positioned with the second substrate such that when the first surface of the second substrate is received by the second surface of the first substrate, the means for electrochemical measurements is at a corresponding measurement position. The means for electrochemical measurements includes at least one electrode monitoring entry of the cells into the chamber, at least one electrode monitoring leaving of the cells from the chamber, and a plurality of electrodes detecting chemical species in the chamber.

The bioreactor further includes a third substrate having a first surface and an opposite, second surface, and means adapted for optical measurements. The means for optical measurements is positioned with the third substrate such that when the first surface of the third substrate is received by the second surface of the first substrate, the means for optical measurements is at a corresponding measurement position. The means for optical measurements includes a plurality of optical sensors strategically positioned for detecting chemical and biological species within the chamber and the physiological state of the cells within the chamber. The third substrate is at least partially transparent.

In yet another aspect, the present invention relates to an inventive bioreactor and its variants. In one embodiment, the bioreactor includes a first substrate having a first surface and an opposite second surface, defining a chamber therebetween for receiving cells and a liquid medium. The first substrate can be fabricated from glass, Mylar, PDMS, silicon, a polymer, a semiconductor, or any combination of them. The bioreactor further includes a second substrate sized such that when the second substrate is received by the first substrate, the chamber is covered.

An inlet port and a first connection channel are formed in the first substrate, where the first connection channel is in fluid communication with the inlet port and the chamber for allowing a stream of substance to be delivered to the chamber. Additionally, an outlet port and a second connection channel are formed in the first substrate, where the second connection channel is in fluid communication with the outlet port and the chamber for allowing a stream of substance to be removed from the chamber.

The bioreactor further has confining means positioned in the chamber to form a confinement region to confine the cells therein. In one embodiment, the confining means includes a first filter and a second filter, where the first filter is positioned proximate to the first connection channel and the second filter is positioned proximate to the second connection channel, and the first filter and the second filter are substantially parallel to each other. Each of the first filter and the second filter includes a plurality of posts spaced apart from each other not to allow cells to pass through it. The distances between two neighboring posts can vary.

The first substrate, further defines a first alternate port and a third connection channel that is in fluid communication with the first alternate port and the confined region of the chamber for allowing seed cells to perfuse only inside the confined region in the chamber.

The bioreactor further includes one or more supporting members positioned outside the confined region of the chamber for supporting the second substrate. Additionally, the bioreactor further includes at least one supporting member positioned inside the confined region of the chamber for supporting the second substrate. Note that the chamber is formed with sidewalls of the chamber are tapered at the intersections of the connection channels with the chamber to form an angle of inclination $\alpha$, which is preferred in the range of about between 10-45° from vertical, and an enclosed angle $\beta$, which is preferred in the range of about between 30-80°, respectively, to reduce shear forces generated by sharp corners.

In a further aspect, the present invention relates to another inventive bioreactor and its variants. In one embodiment, the bioreactor includes a first substrate having a first surface and an opposite second surface, defining a first chamber therebetween for receiving a first type of cells and a liquid medium. One or more second chambers are formed in the first substrate for receiving a second type of cells and a liquid medium.

Moreover, one or more connection channels are formed in the first substrate, wherein each of connection channels is in fluid communication with a corresponding second chamber and the first chamber for allowing the first type of cells and the second type of the cells to interact with each other. For example, connection channel is in fluid communication with a corresponding second chamber and the first chamber. The first type of cells includes protozoa, and the second type of cells includes bacteria.

The connection channels are formed to allow protozoa to travel therein. However, a variety of structures can be utilized to limit the mobility of protozoa for different applications. For example, a size limiting or exclusion post can be utilized to limit the mobility of protozoa, which can be used to evaluate the mobility of protozoa. Alternatively, one of the connection channels formed with a cross-sectional dimension variable along the length of the connection channel can be utilized to limit the mobility of protozoa, which can also be used to evaluate the mobility of protozoa. Moreover, a barrier positioned in a connection channel can be utilized for separation of bacteria and protozoa, which can be used to evaluate protozoa chemotaxis.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIGS. 1A1-3 schematically show a bioreactor according to one embodiment of the present invention: 1A1, a top cross-sectional view; 1A2, a transverse cross-sectional view; and 1A3, a lateral cross-sectional view.

FIGS. 2A1-2 schematically show a bioreactor with multiple traps according to one embodiment of the present invention: 2A1, a perspective view; and 2A2, a perspective sectional view.

FIGS. 3A-D schematically show a top cross-sectional view of a bioreactor with a multi-chamber according to one embodiment of the present invention.

DETAILED DESCRIPTION OF THE INVENTION

Figure 1B:
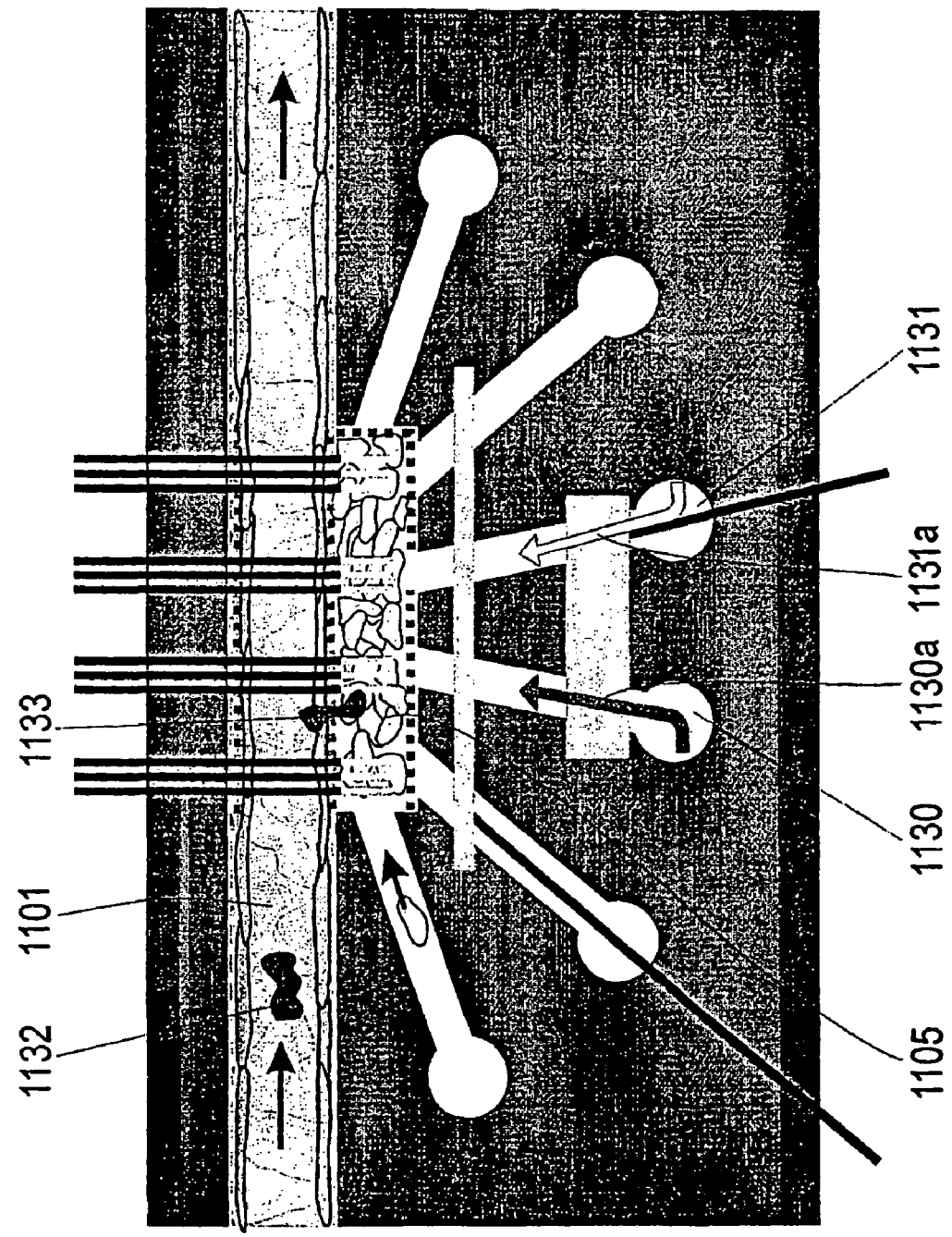
FIG. 1B schematically shows a top cross-sectional view of a bioreactor according to another embodiment of the present invention.

Various embodiments of the invention are now described in detail. Referring to the drawings, like numbers indicate like parts throughout the views unless the context clearly dictates otherwise. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used. For example, conventional techniques of molecular biology, microbiology and recombinant DNA techniques may be employed in accordance with the present invention. Such techniques and the meanings of terms associated therewith are explained fully in the literature. See, for example, Sambrook, Fitsch & Maniatis. Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. L Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994). See also, PCR Protocols: A Guide to Methods and Applications, Innis et al., eds., Academic Press, Inc., New York (1990); Saiki et al., Science 1988, 239:487; and PCR Technology: Principles and Applications for DNA Amplification, H. Erlich, Ed., Stockton Press.

Certain terms that are used to describe the invention are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "molecule" means any distinct or distinguishable structural unit of matter comprising one or more atoms, and includes for example polypeptides and polynucleotides.

As used herein, "cell" means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. As used herein, a cell is generally living unless otherwise indicated. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). Cell or a plurality of cells can also comprise cell lines. Example of cell lines include liver cell, macrophage cell, neuroblastoma cell, endothelial cell, intestine cell, hybridoma, CHO, fibroblast cell lines, red blood cells, electrically excitable cells, e.g. Cardiac cell, myocytes (AT1 cells), cells grown in co-culture, NG108-15 cells (a widely used neuroblastoma X glioma hybrid cell line, ATCC# HB-12317), primary neurons, a primary cardiac myocyte isolated from either the ventricles or atria of an animal neonate, an AT-1 atrial tumor cardiac cell Liver cells are also known as Hepatocytes, Secretory cell (depolarize and it secretes things) pancreatic beta cells secrete insulin, HELA cells (Helen Lane), HEK293 Human Epithial Kidney c, Erythrocytes (primary red blood cells), Lymphocytes and the like. Each cell line may include one or more cells, same or different. For examples, the liver cell comprises at least one of Human hepatocellular carcinoma ("HEPG2") cell, CCL-13 cell, and H4IIE cell, the macrophage cells comprises at least one of peripheral blood mononuclear cells ("PBMC"), and skin fibroblast cells, the neuroblastoma cell comprises a U937 cell, the endothelial cell comprises a human umbilical vein-endothelial cell ("Huv-ec-c"), and the intestine cell comprises a CCL-6 cell.

"Culture" means a growth of living cells in a controlled artificial environment. It may be a culture of microorganisms, such as a bacterial culture, or one of animal or plant cells, such as a tissue culture. The bioreactors according to the invention can do both and more. Cultures require appropriate sources of food and energy, provided by the culture medium, and a suitable physical environment. Tissue cultures can themselves become a culture medium for viruses, which grow only with live cells. Cultures of only one kind of cells are known as pure cultures, as distinguished from mixed or contaminated cultures.

"Tissue" means an aggregation of cells more or less similar morphologically and functionally. The animal body is composed of four primary tissues, namely, epithelium, connective tissue (including bone, cartilage, and blood), muscle, and nervous tissue. The process of differentiation and maturation of tissues is called histogenesis.

A "sensor" is broadly defined as any device that can measure a measurable quantity. For examples, a sensor can be a thermal detector, an electrical detector, a chemical detector, an optical detector, an ion detector, a biological detector, a radioisotope detector, an electrochemical detector, a radiation detector, an acoustic detector, a magnetic detector, a capacitive detector, a pressure detector, an ultrasonic detector, an infrared detector, a microwave motion detector, a radar detector, an electric eye, an image sensor, any combination of them and the like. A variety of sensors can be chosen to practice the present invention.

The term "analyte" means a material that can be consumed or produced by a cell. Examples of analyte of interest include pH, K, oxygen, lactate, glucose, ascorbate, serotonin, dopamine, ammonina, glutamate, purine, calcium, sodium, potassium, NADH, protons, insulin, NO (nitric oxide) and the like.

The term "flow" means any movement of fluid such as a liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a substrate on microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

A "liquid or medium" is a fluid that may contain one or more substances that affecting growth of cells, one or more analytes, or any combination of them. A medium can be provided with one or more analytes to be consumed by one or more cells. A medium can have one or more analytes generated by one or more cells. A medium can also have at the same time one or more analytes to be consumed by one or more cells and one or more analytes generated by one or more cells. A medium may consist of natural materials, such as enzymatic digests, extracts of yeast or beef, milk, potato slices, or chick embryos. Artificial media are prepared by mixing various ingredients according to particular formulas. A complex medium contains at least one crude ingredient derived from a natural material, hence of unknown chemical composition. A chemically defined or synthetic medium is one in which the chemical structure and amount of each component are known.

An "inlet region" is an area of a bioreactor that receives molecules or cells or liquid. The inlet region may contain an inlet port and channel, a well or reservoir, an opening, and other features which facilitate the entry of molecules or cells into the device. A bioreactor may contain more than one inlet region if desired. The inlet region is in fluid communication with the channel and is upstream therefrom.

An "outlet region" is an area of a bioreactor that collects or dispenses molecules or cells or liquid. An outlet region is downstream from a discrimination region, and may contain outlet channels or ports. A bioreactor may contain more than one outlet region if desired.

An "analysis unit" is a microfabricated substrate, e.g., a microfabricated chip, having at least one inlet region, at least one channel and chamber, at least one detection region and at least one outlet region. A device of the invention may comprise a plurality of analysis units.

A "channel" is a pathway of a bioreactor of the invention that permits the flow of molecules or cells to pass a detection region for detection (identification), or measurement. The detection and discrimination regions can be placed or fabricated into the channel. The channel is typically in fluid communication with an inlet port or inlet region, which permits the flow of molecules or cells or liquids into the channel. The channel is also typically in fluid communication with an outlet region or outlet port, which permits the flow of molecules or cells or liquid out of the channel. The channel can also be used as a chamber to grown cells, and vice versa.

A "detection region" or "sensing volume" or "chamber" is a location within the bioreactor, typically in or coincident with the channel (or a portion thereof) and/or in or coincident with a detection loop, where molecules or cells to be grown, identified, characterized, hybridized, measured, analyzed or maintained (etc.), are examined on the basis of a predetermined characteristic. In one embodiment, molecules or cells are examined one at a time. In other embodiments, molecules, cells or samples are examined together, for example in groups, in arrays, in rapid, simultaneous or contemporaneous serial or parallel arrangements, or by affinity chromatography.

"Reaction time" is the time that a system of interest requires to respond to a change. For example, the reaction time of a cell is the time required for at least one of the physiological processes of a cell to adapt or respond to a change in its environment. Each type of cell has its own characteristic reaction time with respect to a particular change in its environment. The reaction time of a sensor is the time required for the sensor to respond to a change in the quantity that it is sensing. For example, the reaction time of an electrochemical sensor is set by the size of the sensor and the thickness and nature of protective coatings on the activated surfaces of the sensor. The reaction time of a microfluidic system is determined by, among other things, the reaction time of the cell to changes in the environment, the time required for chemical species to diffuse throughout the sensing volume, the reaction time of the sensor(s) and the diffusion time of the analyte being controlled by the actuators.

"Bacteria" are extremely small—usually 0.3-2.0 micrometers in diameter—and relatively simple microorganisms possessing the prokaryotic type of cell construction. Each bacterial cell arises either by division of a preexisting cell with similar characteristics, or through combination of elements from two such cells in a sexual process.

"Protozoa" means a group of eukaryotic microorganisms traditionally classified in the animal kingdom. Although the name signifies primitive animals, some Protozoa (phytoflagellates and slime molds) show enough plantlike characteristics to justify claims that they are plants. Protozoa range in size from 1 to $10^6$ micrometers. Colonies are known in flagellates, ciliates, and Sarcodina. Although marked differentiation of the reproductive and somatic zooids characterizes certain colonies, such as Volvox, Protozoa have not developed tissues and organs.

Several embodiments are now described with reference to the FIGS. 1-3, in which like numbers indicate like parts throughout the FIGS. 1-3.

Overview of the Invention

The inventors of the present invention overcome the disadvantages of the prior art and develop new bioreactors that have, among other new and inventive features, the capability of providing controlled chemokine gradients independent of the perfusion flow and allow extravasation of a cellular matrix. Recent advances in the fabrication of nanofilters[57-61] are used to create perfused-membrane bioreactors according to the present invention that allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment.

One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence, the bioreactors according to the present invention can be considered as the next generation of migration bioreactors that may move beyond a simple MicroTransWell (MTW) system to one that more closely replicates in vitro the microenvironment living tissue.

Moreover, the application of microfabrication techniques, microfluidics, and microbiosensors with the bioreactors according to the present invention offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These devices will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Additionally, the limitation of the planar Borenstein design that there is too little surface area of capillaries available to support the growth of a substantial volume of cells is overcome by the present invention, which remedies this problem by creating a multi-layer intercalated supply and return bioreactor that allows the full surface of a planar bioreactor to be covered with capillaries, and hence capillary-perfused cells.

More specifically, in one aspect, the present invention relates to bioreactors. These bioreactors are biomicroelectromechanical systems (BioMEMS) that serve as migration microenvironments to study molecular mechanisms of tumor angiogenesis, tumor metastasis and leukocyte migration, but can also function as more general tissue bioreactors and perfusion systems. Among other things, one unique aspect of these microfluidic devices is their integration of suitable cell culture and microfabrication techniques, which permit cell growth in small, confined, well-perfused volumes at tissue densities, provide independent control of multiple chemokines and growth factor gradients, shear forces, tissue perfusion, and permeability of physical barriers to cellular migration, and allow detailed optical and electrochemical observation of normal and cancerous cells during cell migration, intravasation, extravasation, angiogenesis, and other cellular processes.

Recent advances in the fabrication of nanofilters[57-61] can be used to practice the present invention to provide perfused-membrane bioreactors that can allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment. One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence the next generation of migration bioreactors will eventually move beyond a simple MicroTransWell (MTW) system to one that more closely replicates in vitro the microenvironment living tissue.

The application of microfabrication techniques, microfluidics, and microbiosensors offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These bioreactors will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Without intent to limit the scope of the invention, exemplary devices, application of them and related observations according to the embodiments of the present invention are given below. Note that titles or subtitles may be used in the examples for convenience of a reader, which in no way should limit the scope of the invention. Moreover, certain theories may have been proposed and disclosed herein; however, in no way they, whether they are right or wrong, should limit the scope of the invention so long as the devices and applications of them are practiced according to the invention without regard for any particular theory or scheme of action.

EXAMPLES

Capillary Bioreactor

Referring now to FIGS. 1(A-D), the present invention can be practiced in association with an inventive bioreactor 1100 and its variants as shown in FIGS. 1(A-D). In one embodiment, referring first to FIGS. 1A1, 1A2 and 1A3, the bioreactor 1100 includes a first substrate 1124 having a first surface 1124a, an opposite second surface 1124b and edges. The bioreactor 1100 further includes a second substrate 1121 having a first surface 1121a and an opposite second surface 1121b, defining a cavity 1121c with a bottom surface 1121d, where the bottom surface 1121d is located therebetween the first surface 1121a and the second surface 1121b. The first surface 1124a of the first substrate 1124 is received by the second surface 1121b of the second substrate 1121 to cover the cavity 1121c so as to form a channel 1101 for receiving cells and a liquid medium. The second substrate 1121 can be fabricated from glass, Mylar, PDMS, silicon, a polymer, a semiconductor, or any combination of them. The first substrate 1124 is at least partially optically transparent such that the dynamic activities of cells in the channel 1101 are detectable through optical detecting means.

A recess 1105c is formed in the second substrate 1121 with a bottom surface 1105d and in fluid communication with the channel 1101. Additionally, a barrier 1106 is positioned for covering the recess 1105c so as to form an outer chamber 1105. The barrier 1006 has a porosity to allow the channel 1101 and the outer chamber 1105 to be in fluid communication and control the move of at least one predetermined type of cells between the channel 1101 and the outer chamber 1105. In one embodiment as best shown in FIG. 1A1, the barrier 1106 includes a plurality of posts spaced with a gap from each other. These posts may be coated in certain locations with substances to prevent entry of cells, particularly the endothelial cells. Gaps between the posts in certain locations allow for delivery of particular cell types to the outer chamber 1105.

The second substrate 1121 further defines a first opening 1101a and an opposite, second opening 1101b adapted for allowing a flow of liquid to be introduced into the channel 1101 through the first opening 1101a and away from the channel 1101 through the second opening 1101b substantially along a first direction 1101c.

The bioreactor 1100 further includes a biocompatible coating layer 1102 applied to the interior surfaces of the second substrate 1121 around the channel 1101. The biocompatible coating layer 1102 includes a material that may inhibit cell adhesion to the biocompatible coating layer, enhance cell adhesion to the biocompatible coating layer, promote organization and growth of cells, or function as a fluorescent marker or indicator of the state of cells.

In forming the bioreactor 1100, the channel 1101 is sized to allow the growth of a layer of cells 1103 on the biocompatible coating layer 1102 and the flow of liquid in the channel 1101. The flow of liquid is controlled so as to provide a known shear force to the layer of cells 1103. The flow of liquid can be further controlled so as to provide an environment that simulates a vascular space in the channel 1101. For examples, the channel 1101 can be used for introduction of endothelial cells, and for their subsequent perfusion.

The cells can be any type of living cells, including, but not limited to, bacteria, protozoa, or both, normal cells, endothelial cells, tumor cells, or any combination of them. Cells can be introduced into the channel 1101 individually, in a collection of cells, or in the form of biofilm. In one embodiment, the layer of cells 1103 substantially forms an endothelial cells lined capillary in the channel 1101. The channel 1101 is sized such that when at least one cell 1104 that is not one of the endothelial cells, such as a tumor cell, is introduced into the channel 1101, it can undergo intravasation in the endothelial cells lined capillary.

Figure 1C:
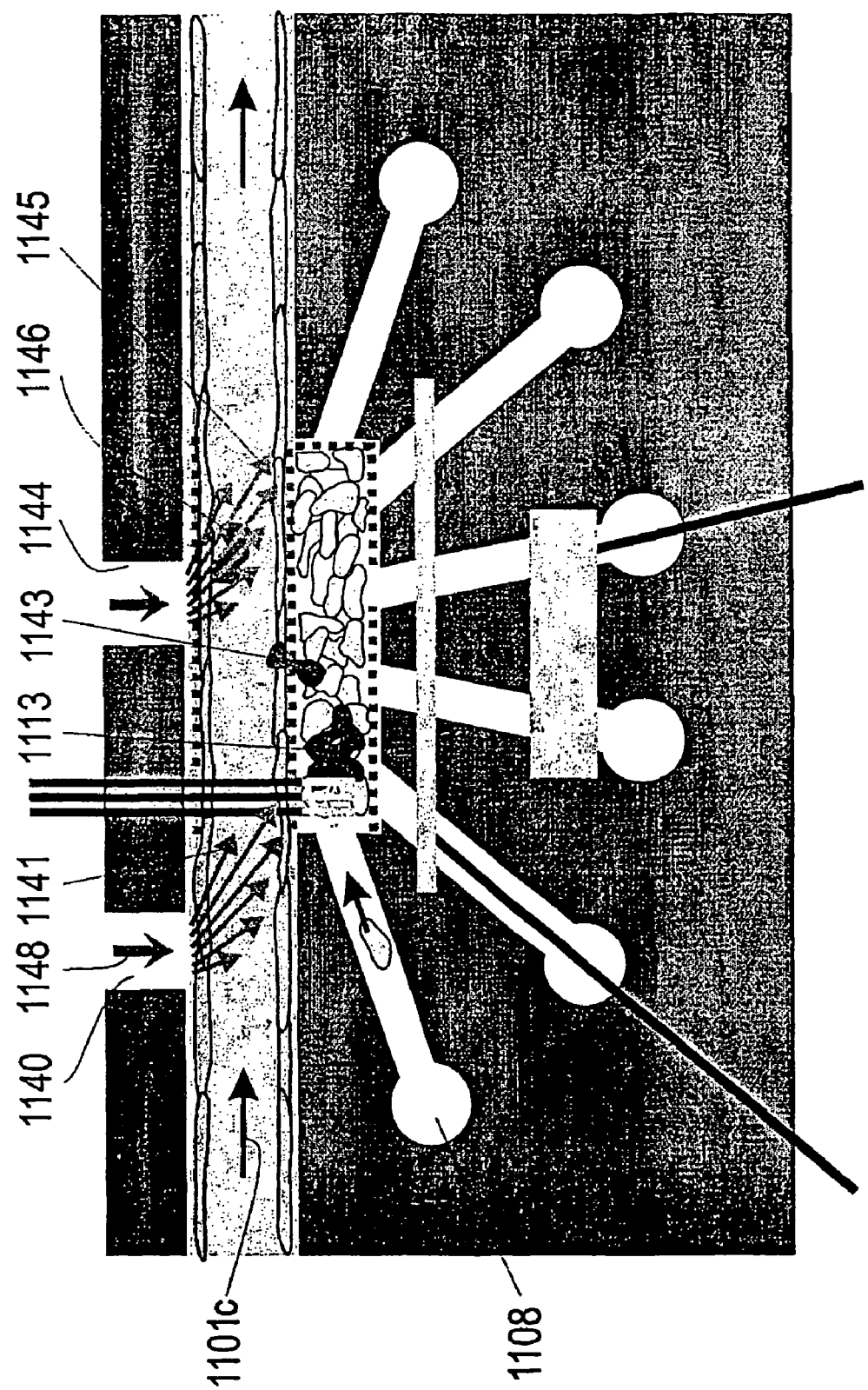
FIG. 1C schematically shows a top cross-sectional view of a bioreactor according to yet another embodiment of the present invention.

In an alternative embodiment as shown in FIG. 1C, the second substrate 1121 further defines one or more injection ports 1140, 1141 in fluid communication with the channel 1101 to allow a stream of substance to be introduced into the channel 1101 through the injection port 1140, 1141 substantially along a second direction 1148, respectively. As shown in FIG. 1C, the second direction 1148 is substantially perpendicular to the first direction 1101c. The stream of substance is controlled so as to provide a gradient to the channel 1101. The stream of substance includes a substance affecting the growth of cells such as chemokine.

Referring now to FIGS. 1A1, 1A2 and 1A3, the outer chamber 1105 is sized to allow the growth of a host of cells. The host of cells includes at least a first type of cells 1107 and a second type of cells 1113 that is different from the first type of cells 1107. In other words, the outer chamber 1105 is sized to allow the growth of two types of cells. In one embodiment, the first type of cells 1107 includes normal cells, and the second type of cells 1113 includes tumor cells. These host cells can either be grown in the outer chamber 1105, or so as to avoid undesired growth of endothelial cells into the host cell population, they may be grown on a suitable substrate outside of the bioreactor 1100 and then be introduced as a complete unit or smaller units into the outer chamber 1105 either through one of the microfluid ports or by temporary removal of the fist substrate 1124 such as a glass lid of the outer chamber 1105. As best shown in FIG. 1A2, a port 1122 and a connection channel 1123 are formed in the second substrate 1121 such that the connection channel 1123 is in fluid communication with the outer chamber 1105 and the port 1122. The bioreactor 1100 further includes a plurality of electrodes 1114, 1115, 1116 adapted for electrochemical measurements of the host of cells. Moreover, the bioreactor 1100 further includes a plurality of controlling ports 1108, 1109, 1110 and a plurality of connection channels 1108a, 1109a, 1110a, wherein each of the connection channels 1108a, 1109a, 1110a is in fluid communication with a corresponding one of controlling ports 1108, 1109, 1110 and the outer chamber 1105, respectively.

Bioreactor 1100 and its variants as given above can find many applications. Such a readily fabricated device is suitable for events that are high-probability and in relatively short lengths of capillary, such as neutrophil binding to a tube of activated endothelial cells. Multiple channels/ports allow delivery of different cells, and establishment of chemokine, nutrient, and pH gradients. Electrodes measure metabolism. Hence it may best suited for experiments or applications involving activated or inflamed endothelial cells.

For example, as shown in FIG. 1B, bioreactor 1100 is used as a capillary perfused migration bioreactor for the study of cancer cell or neutrophil extravasation in the presence of two competing chemokine gradients. In particular, a first stream 1130a of chemokine is injected through a port 1130 and hence creates a first gradient of that chemokine both in the outer chamber 1105 and the channel 1101. Additionally, a second stream 1131a of chemokine is injected through a port 1131 and hence creates a second gradient of that chemokine both in the outer chamber 1105 and the channel 1101. A spectrum of dynamics of the cells may happen. For instances, a cancer cell or a neutrophil 1132 moves along the channel 1101 in response to either perfusion flow or the presence of the first and second chemokine gradients, and a cancer cell or neutrophil 1133 undergoes extravasation from the channel 1101 into the outer chamber 1105.

Figure 1D:
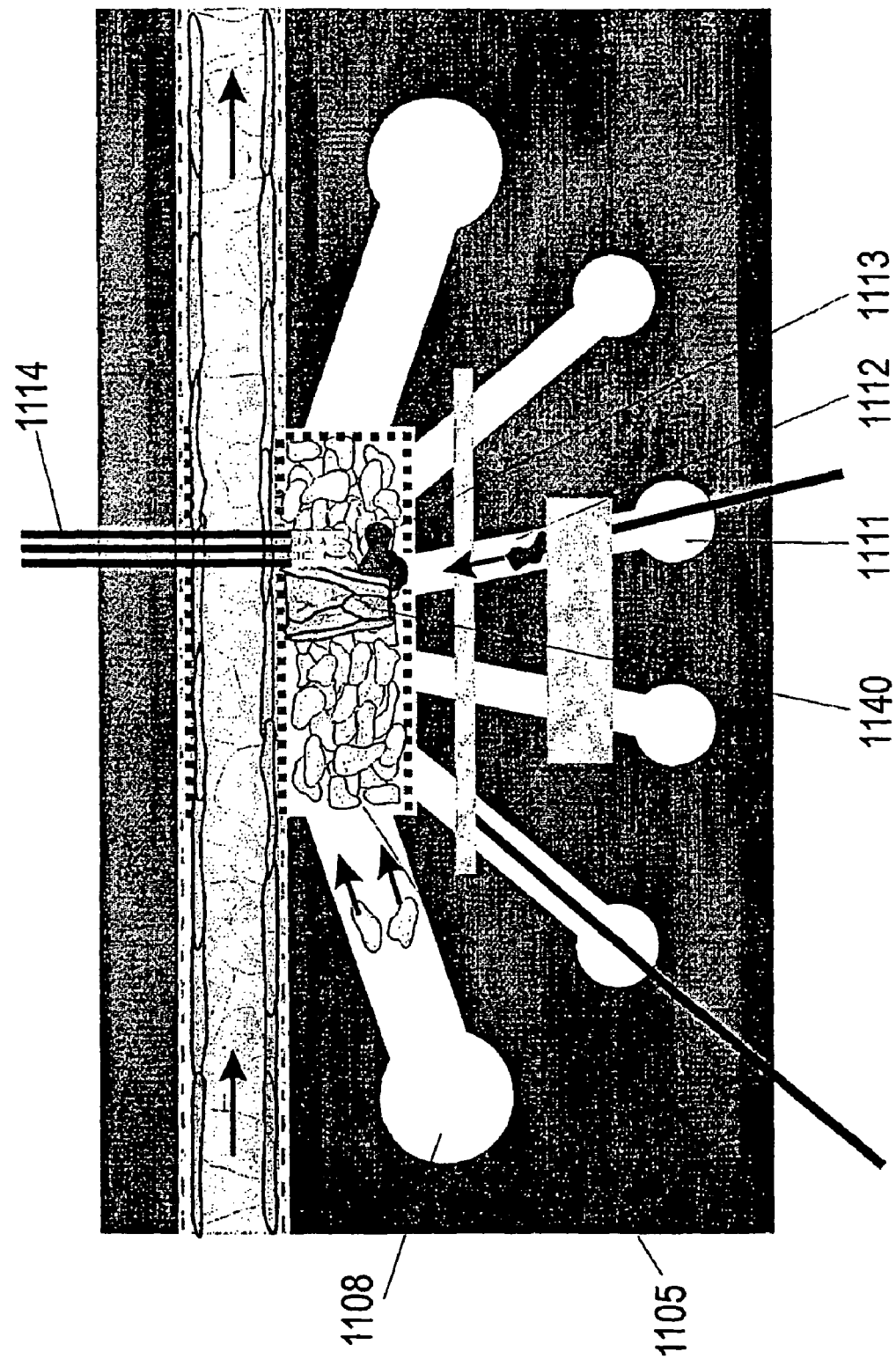
FIG. 1D schematically shows a top cross-sectional view of a bioreactor according to a further embodiment of the present invention.

FIG. 1D illustrates another application. Here bioreactor 1100 is used as a capillary perfused migration bioreactor for the study endothelial tube formation triggered by chemokine excreted by tumor cells, where the outer chamber 1105 of sufficient size contain a sufficiently larger volume of host cells 1108 that is required to ensure endothelial tube formation. An endothelial tube 1140 is formed in response to either chemokine being released by the tumor cells 1113, or by microfluidic delivery of vascular endothelial growth factor (VEGF) or other substances through the microfluidic port 1111. Note that another tumor cell 1112 is on the move. The electrodes 1114 may be able to detect changes in the extracellular environment associated with tube formation and the associated proteolysis.

Bioreactor with Multiple Traps

Referring now to FIGS. 2(A-I), the present invention can also be practiced in association with an inventive bioreactor 1000 and its variants as shown in FIGS. 2(A-I). In one embodiment, referring first to FIGS. 2A, 10B, 10G, 10H and 10I, the bioreactor 1000 includes a first substrate 1001 having a first surface 1001a and an opposite second surface 1001b, defining a chamber 1006 therebetween for receiving cells 1008 and a liquid medium. The first substrate 1001 can be fabricated from glass, Mylar, PDMS, silicon, a polymer, a semiconductor, or any combination of them.

An inlet port 1021 and a first connection channel 1021a are formed in the first substrate 1001, where the first connection channel 1021a is in fluid communication with the inlet port 1021 and the chamber 1006 for allowing a stream of substance to be delivered to the chamber 1006. Additionally, an outlet port 1005 and a second connection channel 1005a are formed in the first substrate 1001, where the second connection channel 1005a is in fluid communication with the outlet port 1005 and the chamber 1006 for allowing a stream of substance to be removed from the chamber 1006.

Moreover, as best shown in the insert of FIG. 2A, the bioreactor 1000 has confining means 1003 positioned in a region in the chamber 1006 proximate to the first connection channel 1021a to confine the cells 1008. In one embodiment, the confining means 1003 includes a plurality of traps 1007, where each of the plurality of traps 1007 is capable of receiving at least one cell or a collection of cells 1008. Each of the plurality of traps 1007 includes a structure defining a recess 1007a so as to receive and confine one or more cells 1008 therein. The structure may be partially formed with a filter 1007b to allow the recess 1007a to be in fluid communication with the chamber 1006. The filter 1007b can be formed with a plurality posts spacing from each other with a gap g. Traps can take various shapes and have different physics properties. For examples, in the embodiment as shown in FIG. 2G, a trap 1090 has distinct posts and sides. In the embodiment as shown in FIG. 2H, a trap 1092 has posts and sides that are extending to the posts. And in the embodiment as shown in FIG. 2I, a trap 1093 is formed with a single post and sides. The plurality of traps 1007 can be arranged to form an array.

Additionally, the first substrate 1001 defines a first alternate port 1022 and a third connection channel 1022a in fluid communication with the first alternate port 1022 and the first connection channel 1021a for allowing additional substance to be introduced into the chamber 1006. Moreover, the first substrate 1001 further defines a second alternate port 1011, a third connection channel 1011a, and a second chamber 1009, wherein the third connection channel 1011a is in fluid communication with second alternate port 1011 and the second chamber 1009, and the second chamber 1009 is in fluid communication with the first connection channel 1021a. Furthermore, the second chamber 1009 is formed with an oxygen permeable structure to provide oxygen to the cells.

Figure 2B:
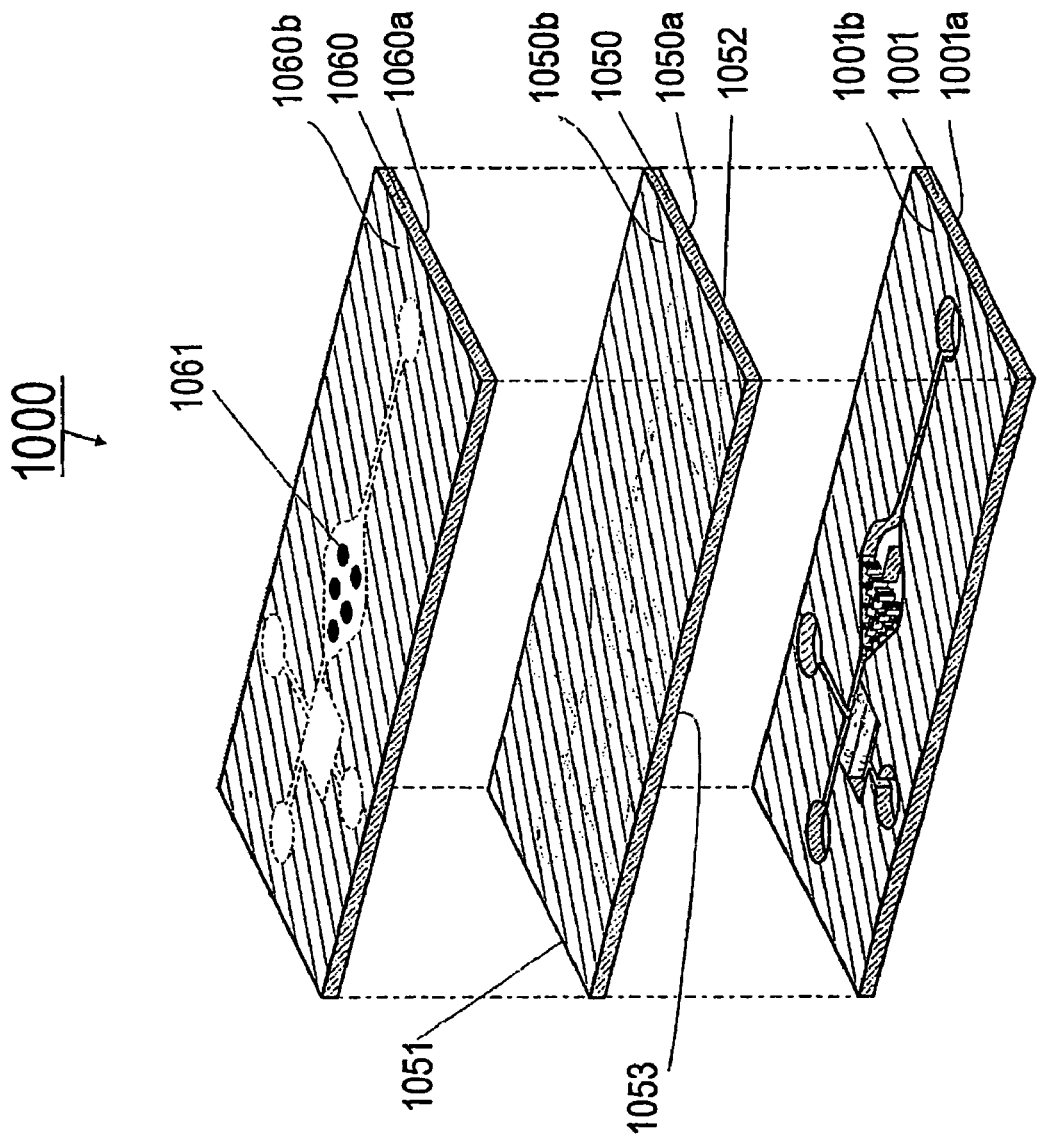
FIG. 2B schematically shows a perspective view of a bioreactor with multiple traps according to another embodiment of the present invention.

Referring now to FIG. 2B, the bioreactor 1100 further includes a second substrate 1050 having a first surface 1050a and an opposite, second surface 1050b, and means adapted for electrochemical measurements of the cells in the chamber 1006. The means for electrochemical measurements is positioned with the second substrate 1050 such that when the first surface 1050a of the second substrate 1050 is received by the second surface 1001b of the first substrate 1001, the means for electrochemical measurements is at a corresponding measurement position. The means for electrochemical measurements includes at least one electrode 1051 monitoring entry of the cells into the chamber 1006, at least one electrode 1052 monitoring leaving of the cells from the chamber 1006, and a plurality of electrodes 1053 detecting chemical species in the chamber 1006.

The bioreactor 1000 further includes a third substrate 1060 having a first surface 1060a and an opposite, second surface 1060b, and means adapted for optical measurements. The means for optical measurements is positioned with the third substrate 1060 such that when the first surface 1060a of the third substrate 1060 is received by the second surface 1001b of the first substrate 1001, the means for optical measurements is at a corresponding measurement position. The means for optical measurements includes a plurality of optical sensors 1061 strategically positioned for detecting chemical and biological species within the chamber 1006 and the physiological state of the cells within the chamber 1006. The third substrate 1060 is at least partially transparent.

Bioreactor with Confined Region

Referring now to FIGS. 2(C-F), the present invention can also be practiced in association with an inventive bioreactor 1000 and its variants as shown in FIGS. 2(C-F). In one embodiment, referring first to FIGS. 2C, 2D, 2E and 2F, the bioreactor 1000 includes a first substrate 1001 having a first surface 1001a and an opposite second surface 1001b, defining a chamber 1006 therebetween for receiving cells 1008 and a liquid medium. The first substrate 1001 can be fabricated from glass, Mylar, PDMS, silicon, a polymer, a semiconductor, or any combination of them. The bioreactor 1000 further includes a second substrate (not shown) sized such that when the second substrate 1050 received by the first substrate 1001, the chamber 1006 is covered.

An inlet port (not shown) and a first connection channel 1021a are formed in the first substrate 1001, where the first connection channel 1021a is in fluid communication with the inlet port (not shown) and the chamber 1006 for allowing a stream of substance to be delivered to the chamber 1006.

Additionally, an outlet port (not shown) and a second connection channel 1005a are formed in the first substrate 1001, where the second connection channel 1005a is in fluid communication with the outlet port (not shown) and the chamber 1006 for allowing a stream of substance to be removed from the chamber 1006.

The bioreactor 1000 further has confining means positioned in the chamber 1006 to form a confinement region 1006a to confine the cells 1008 therein. In one embodiment, the confining means includes a first filter 1085a and a second filter 1085b, where the first filter 1085a is positioned proximate to the first connection channel 1021 and the second filter 1085b is positioned proximate to the second connection channel 1005a, and the first filter 1085a and the second filter 1085b are substantially parallel to each other. Each of the first filter 1085a and the second filter 1085b includes a plurality of posts 1086 spaced apart from each other not to allow cells to pass through it. The distances between two neighboring posts can vary. For examples, posts 1086, 1086a, 1088 and 1089, as shown in FIGS. 2C, 2D, 2E and 2F, show them with different gaps, respectively.

Figure 2C:
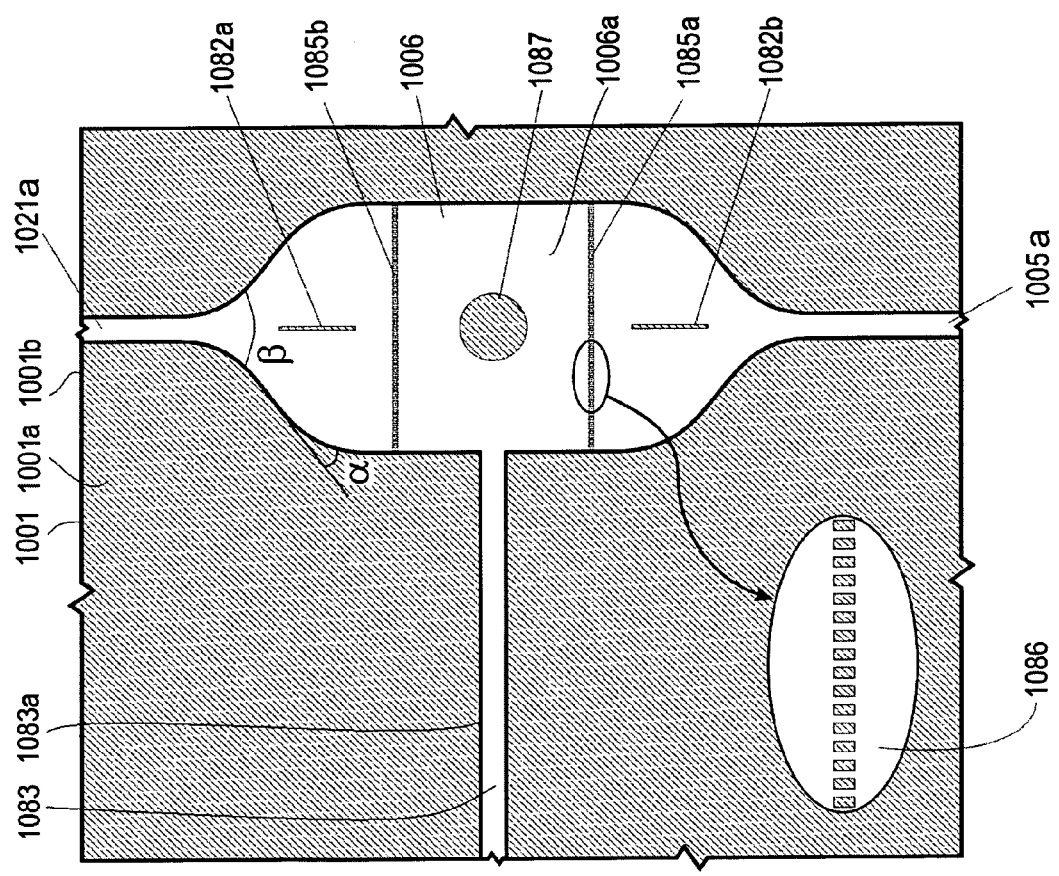
FIG. 2C schematically shows a top cross-sectional view of a bioreactor with a confined region according to one embodiment of the present invention.
Figure 2D:
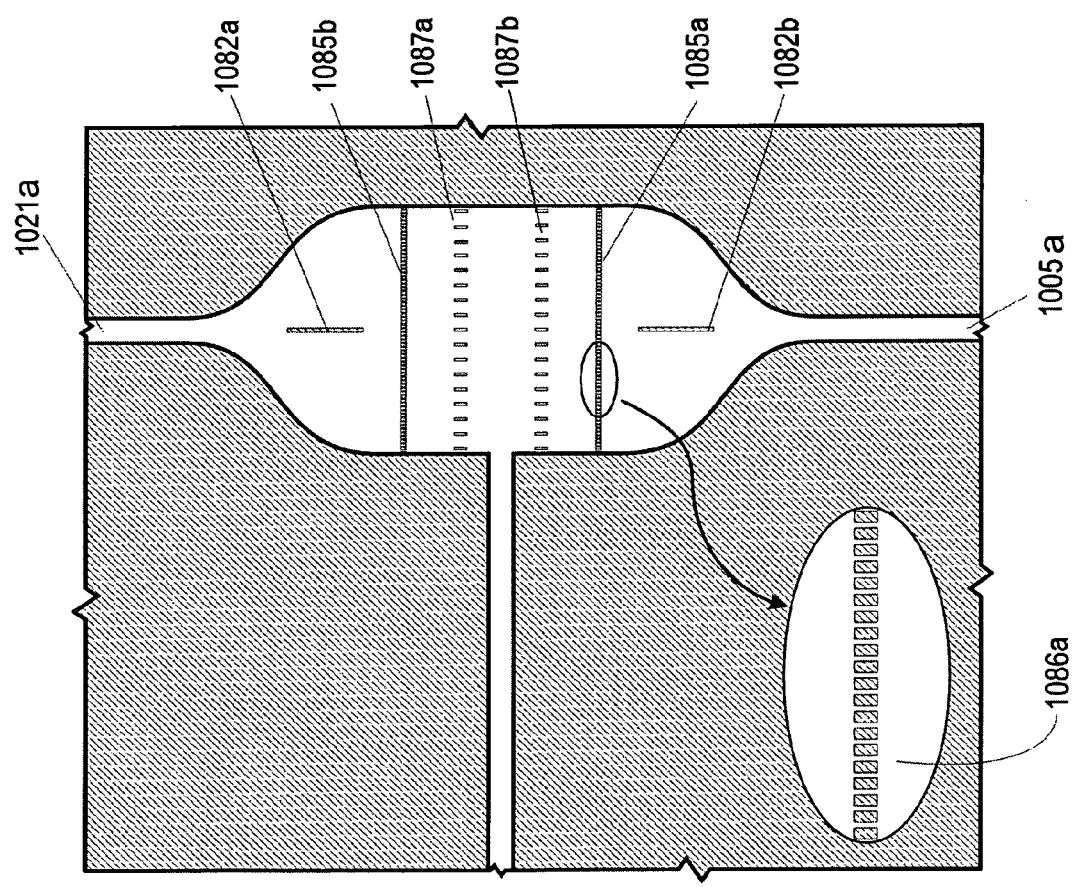
FIG. 2D schematically shows a top cross-sectional view of a bioreactor with a confined region according to another embodiment of the present invention.
Figure 2E:
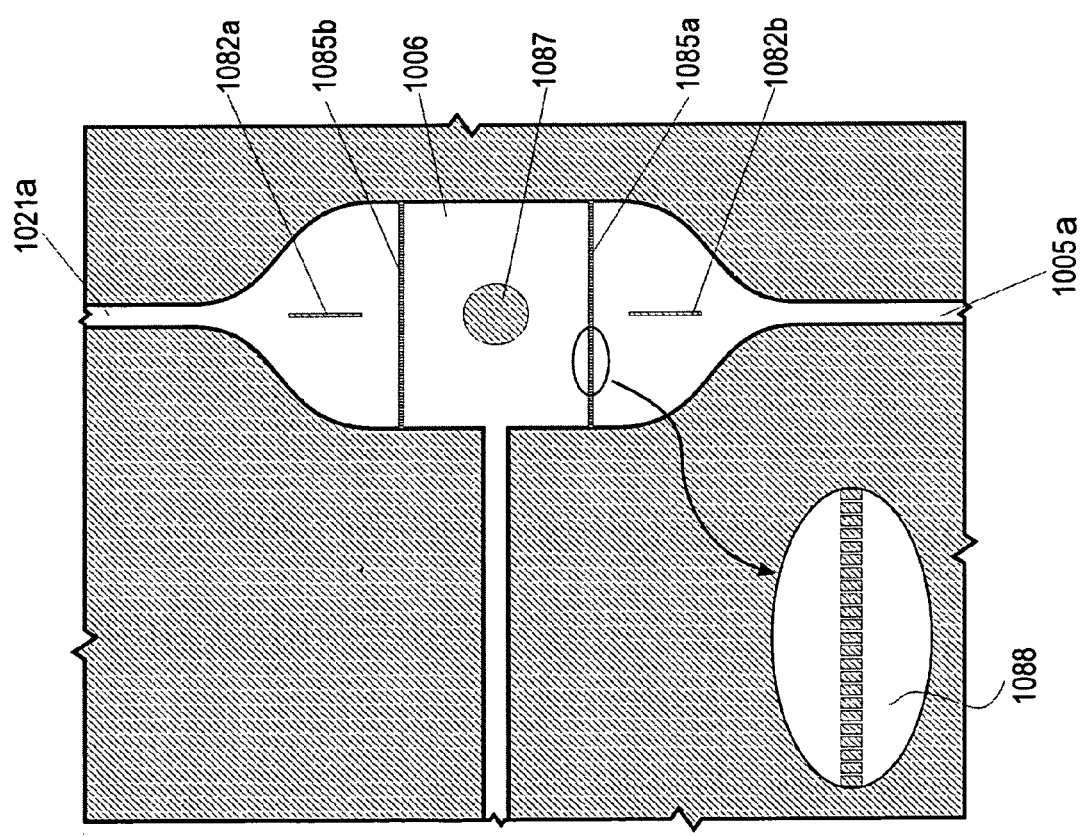
FIG. 2E schematically shows a top cross-sectional view of a bioreactor with a confined region according to yet another embodiment of the present invention.
Figure 2F:
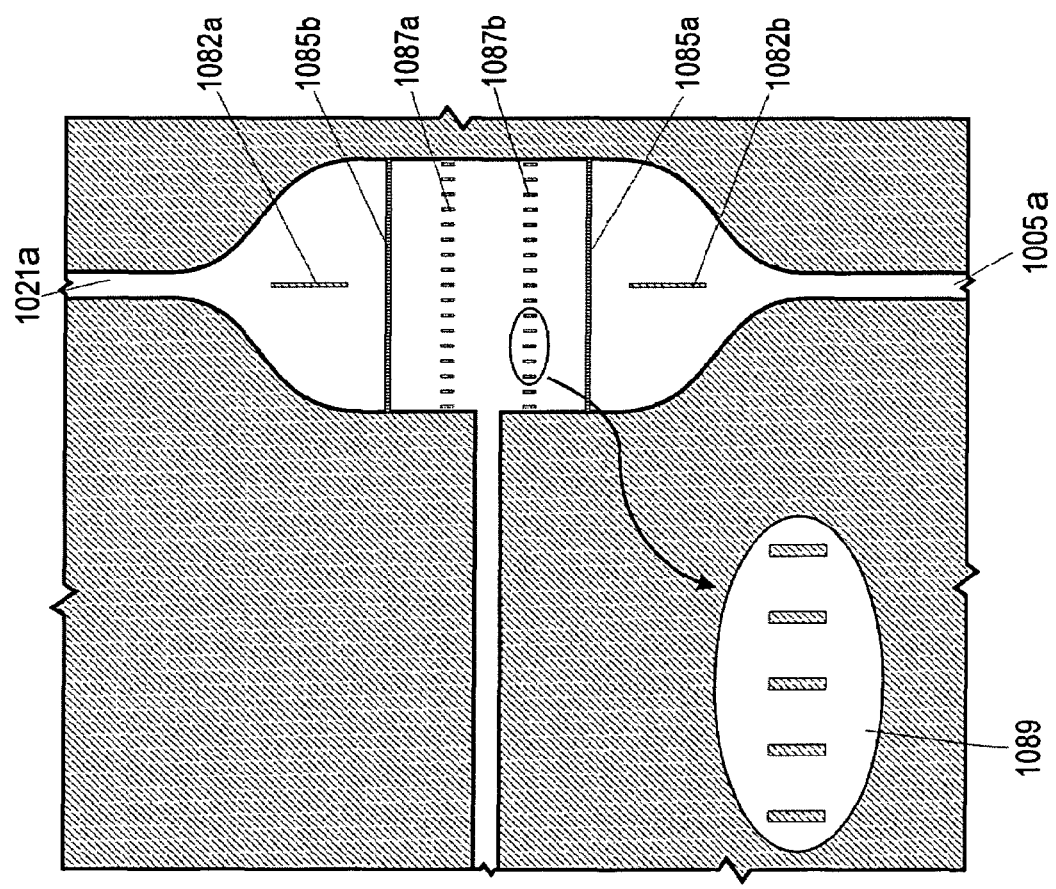
FIG. 2F schematically shows a top cross-sectional view of a bioreactor with a confined region according to a further embodiment of the present invention.
Figure 2G:
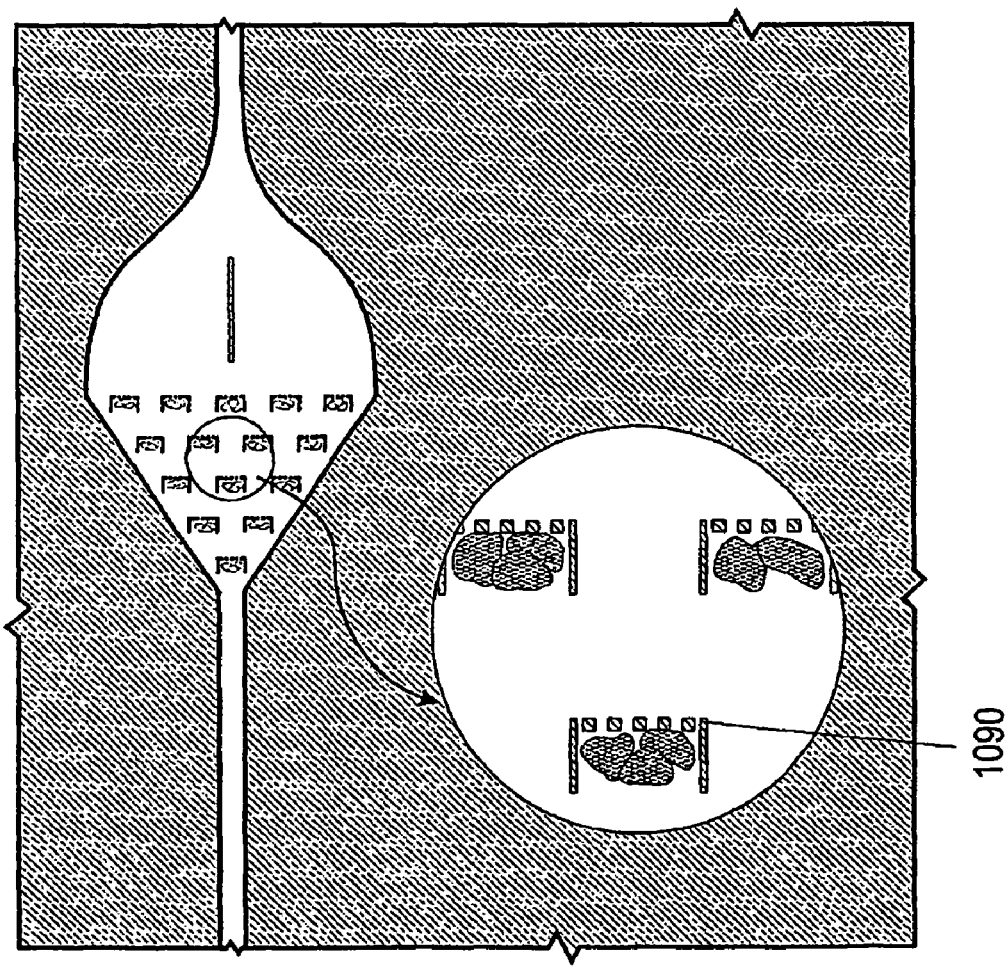
FIG. 2G schematically shows a top cross-sectional view of a bioreactor with multiple traps according to one embodiment of the present invention.
Figure 2H:
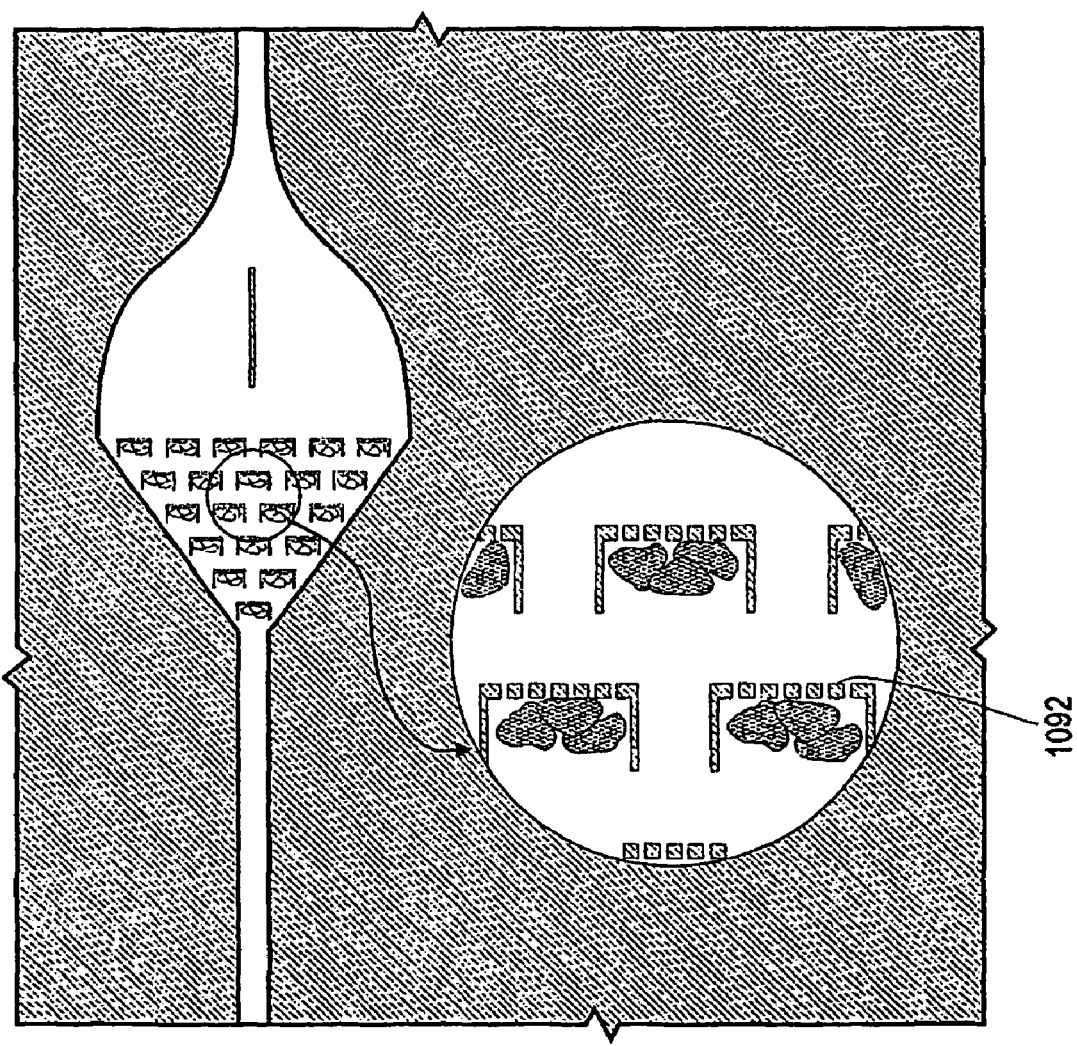
FIG. 2H schematically shows a top cross-sectional view of a bioreactor with multiple traps according to another embodiment of the present invention FIG. 2I schematically shows a top cross-sectional view of a bioreactor with multiple traps according to yet another embodiment of the present invention.
Figure 21:
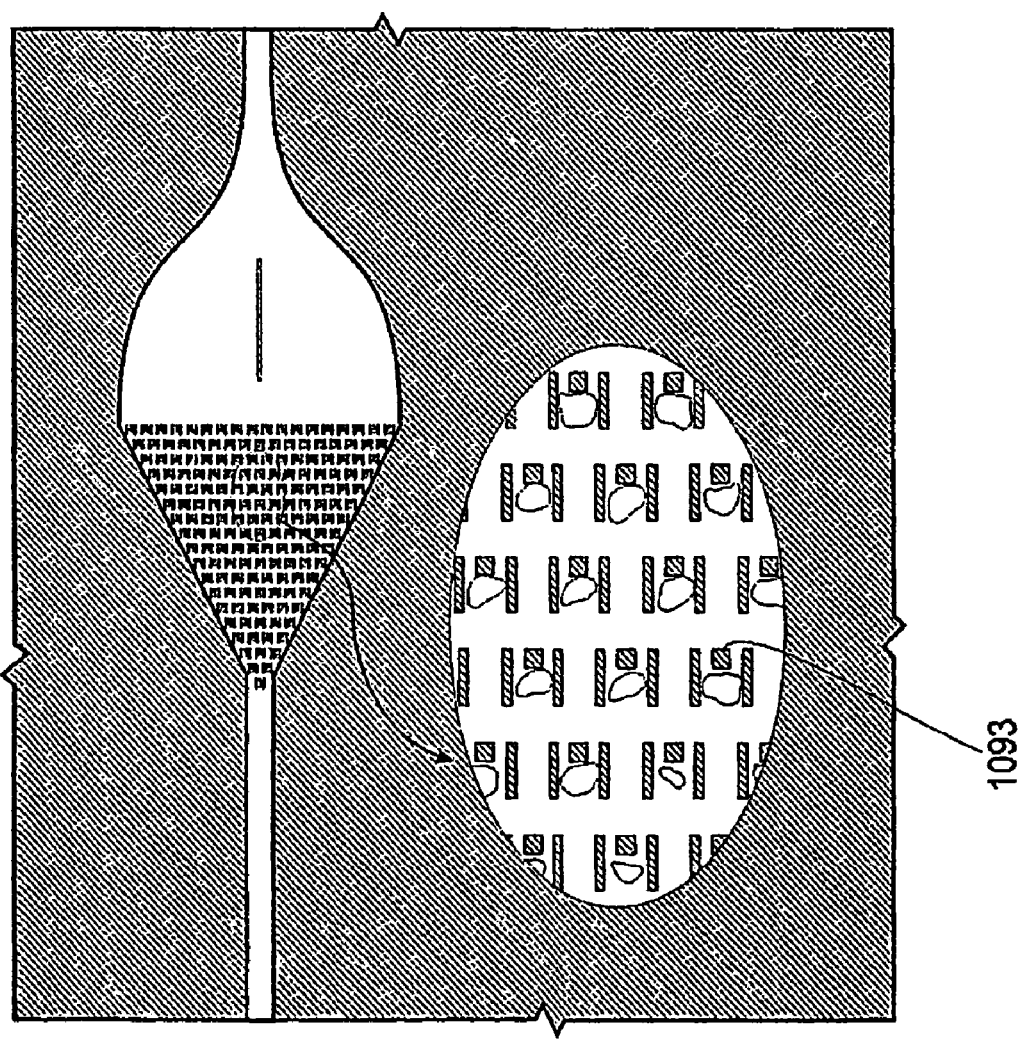

The first substrate 1001, referring now to FIG. 2C, further defines a first alternate port 1083 and a third connection channel 1083a that is in fluid communication with the first alternate port 1083 and the confined region 1006a of the chamber 1006 for allowing seed cells to perfuse only inside the confined region 1006a in the chamber 1006.

The bioreactor 1000 further includes one or more supporting members 1082a, 1082b positioned outside the confined region 1006a of the chamber 1006 for supporting the second substrate 1050. Additionally, the bioreactor 1000 further includes at least one supporting member 1087 positioned inside the confined region 1006a of the chamber 1006 for supporting the second substrate 1050. Note that the chamber 1006 is formed with sidewalls of the chamber 1006 are tapered at the intersections of the connection channels with the chamber 1006 to form an angle of inclination $\alpha$, which is preferred in the range of about between 10-45° from vertical, and an enclosed angle $\beta$, which is preferred in the range of about between 30-80°, respectively, to avoid shear forces generated by sharp corners.

Bioreactor with Multiple Chambers

Referring now to FIGS. 3(A-D), the present invention can also be practiced in association with an inventive bioreactor 800 and its variants as shown in FIGS. 3(A-D). In one embodiment, referring first to FIG. 3A, the bioreactor 800 includes a first substrate 801 having a first surface and an opposite second surface, defining a first chamber 812 therebetween for receiving a first type of cells and a liquid medium. One or more second chambers 811a, 811b, 811c, 811d are formed in the first substrate 801 for receiving a second type of cells and a liquid medium. Moreover, one or more connection channels 813a, 813b, 813c, 813d are formed in the first substrate 801, wherein each of connection channels 813a, 813b, 813c, 813d is in fluid communication with a corresponding second chamber 811a, 811b, 811c, 811d and the first chamber 812 for allowing the first type of cells and the second type of the cells to interact with each other. For example, connection channel 813a is in fluid communication with a corresponding second chamber 811a and the first chamber 812. The first type of cells includes protozoa, and the second type of cells includes bacteria.

The connection channels 813a, 813b, 813c, 813d are formed to allow protozoa to travel therein. However, a variety of structures can be utilized to limit the mobility of protozoa for different applications. For examples, in an embodiment 804 as shown in FIG. 3B, a sizing limiting or exclusion post 805 is utilized to limit the mobility of protozoa, which can be used to evaluate the mobility of protozoa Alternatively, in an embodiment 807 as shown in FIG. 3C, one of the connection channels 813a, 813b, 813c, 813d is formed with a cross-sectional dimension 808 variable along the length of the connection channel is utilized to limit the mobility of protozoa, which can also be used to evaluate the mobility of protozoa. Moreover, in an embodiment 809 as shown in FIG. 3D, a barrier 810 positioned in a connection channel is utilized for separation of bacteria and protozoa, which can be used to evaluate protozoa chemotaxis.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention as is particularly set forth in the claims. Furthermore, the embodiments described above are only intended to illustrate the principles of the present invention and are not intended to limit the claims to the disclosed elements. Indeed, since many embodiments of the invention can be made without departing from the spirit and scope of the invention, the invention resides in the claims hereinafter appended.

LIST OF REFERENCES

1. Godbey, W. T. and Atala, A., In Vitro Systems for Tissue Engineering, Ann. N.Y., Acad.Sci., 961, 10-26, 2002.
2. Murdin, A. D., Thorpe, J. S., Kirkby, N., Groves, D. J., Spier, R. E., Immobilisation and Growth of Hybridomas in Packed Beds, In: Bioreactors and biotransformations, Moody, G. W. and Baker, P. B., eds. Elsevier Applied Science Publishers, London, New York, 99-110, 1987.
3. De Bartolo, L., Jarosch-Von Schweder, G., Haverich, A., Bader, A., A Novel Full-Scale Flat Membrane Bioreactor Utilizing Porcine Hepatocytes: Cell Viability and Tissue-Specific Functions, Biotechnol. Prog., 16, 102-108, 2000.
4. McDuffie, N. G., Cell Culture Bioreactors. In: Bioreactor Design Fundamentals, Butterworth-Heinemann, Boston, 93-119, 1991.
5. Drioli, E, et al., Biocatalytic Membrane Reactors, Applications in Biotechnology and the Pharmaceutical Industry, Taylor & Francis, London, Philadelphia, 1999.
6. Labecki, M., Bowen, B. D., Piret, J. M., Protein Transport in Ultrafiltration Hollow-Fiber Bioreactors for Mammalian Cell Culture, In: Membrane Separations in Biotechnology, Wang, W. K., ed., M. Dekker, New York, 1-62, 2001.
7. Nollert, M. U., Diamond, S. L., McIntire, L. V., Hydrodynamic Shear-Stress and Mass-Transport Modulation of Endothelial-Cell Metabolism, Biotechnol. Bioeng., 38, 588-602, 1991.
8. Augenstein, D. C., Sinskey, A. J., Wang, D. I. C., Effect of Shear on Death of Two Strains of Mammalian Tissue Cells, Biotechnol. Bioeng., 13, 409-418, 1971.
9. Millward, H. R., Bellhouse, B. J., Sobey, I. J., The Vortex Wave Membrane Bioreactor: Hydrodynamics and Mass Transfer, Chemical Engineering Journal and the Biochemical Engineering Journal, 62, 175-181, 1996.
10. Beeton, S., Bellhouse, B. J., Knowles, C. J., Millward, H. R., Nicholson, A. M., Wyatt, J. R., A Novel Membrane Bioreactor for Microbial-Growth, Appl. Microbiol. Biotechnol., 40, 812-817, 1994.
11. Hu, W. S. and Aunins, J. G., Large-Scale Mammalian Cell Culture, Curr. Opin. Biotechnol., 8, 148-153, 1997.
12. Tobert, W. R., Lewis, C. Jr., White, P. J., Feder, J., Perfusion Culture Systems for Production of Mammalian Cell Biomolecules, In: Large-Scale Mammalian cell culture, Feder, J. and Tolbert, W. R., eds., Academic Press, Orlando, 97-123, 1985.
13. Voisard, D., Meuwly, F., Ruffieux, P. A., Baer, G., Kadouri, A., Potential of Cell Retention Techniques for Large-Scale High-Density Perfusion Culture of Suspended Mammalian Cells, Biotechnol. Bioeng., 82, 751-765, 2003.
14. MacNeill, B. D., Pomerantseva, I., Lowe, H. C., Oesterle, S. N., Vacanti, J. P., Toward a New Blood Vessel, Vasc. Med., 7, 241-246, 2002.
15. Wu, H. K, Odom, T. W., Chiu, D. T., Whitesides, G. M., Fabrication of Complex Three-Dimensional Microchannel Systems in PDMS, J. Am. Chem. Soc., 125, 554-559, 2003.
16. Griffith, L. G., Emerging Design Principles in Biomaterials and Scaffolds for Tissue Engineering, Reparative Medicine: Growing Tissues and Organs, 961, 83-95, 2002.
17. Snyder, J. D. and Desai, T. A., Fabrication of Multiple Microscale Features on Polymer Surfaces for Applications in Tissue Engineering, Biomedical Microdevices, 3, 293-300, 2001.
18. S. Solan, A., Prabhakar, V., Niklason, L., Engineered Vessels: Importance of the Extracellular Matrix, Transplant. Proc., 33, 66-68, 2001.
19. Griffith, L. G. and Naughton, G., Tissue Engineering—Current Challenges and Expanding Opportunities, Science, 295, 1009-+, 2002.
20. Powers, M. J., Domansky, K., Kaazempur-Mofrad, M. R., Kalezi, A., Capitano, A., Upadhyaya, A., Kurzawski, P., Wack, K. E., Stolz, D. B., Kamm, R., Griffith, L. G., A Microfabricated Array Bioreactor for Perfused 3D Liver Culture, Biotechnol. Bioeng., 78, 257-269, 2002.
21. Park, T. H. and Shuler, M. L, Integration of Cell Culture and Microfabrication Technology, Biotechnol. Prog., 19, 243-253, 2003.
22. Borenstein, J. T., Terai, H., King, K. R., Weinberg, E. J., Kaazempur-Mofrad, M. R., Vacanti, J. P., Microfabrication Technology for Vascularized Tissue Engineering, Biomedical Microdevices, 4, 167-175, 2002.
23. Kaihara, S., Borenstein, J., Koka, R., Lalan, S., Ochoa, E. R., Ravens, M., Pien, H., Cunningham, B., Vacanti, J. P., Silicon Micromachining to Tissue Engineer Branched Vascular Channels for Liver Fabrication, Tissue Eng., 6, 105-117, 2000.
24. Allen, J. W. and Bhatia, S. N., Improving the Next Generation of Bioartificial Liver Devices, Seminars in Cell & Developmental Biology, 13, 447-454, 2002.
25. Passeraub, P. A., Almeida, A. C., Thakor, N. V., Design, Microfabrication and Analysis of a Microfluidic Chamber for the Perfusion of Brain Tissue Slices, Biomedical Microdevices, 5, 147-155, 2003.
26. Fink, C., Ergun, S., Kralisch, D., Remmers, U., Weil, J., Eschenhagen, T., Chronic Stretch of Engineered Heart Tissue Induces Hypertrophy and Functional Improvement, FASEB J., 14, 669-679, 2000.
27. Mooney, D. T., Mazzoni, C. L., Breuer, C., McNamara, K., Hem, D., Vacanti, J. P., Langer, R., Stabilized Polyglycolic Acid Fibre Based Tubes for Tissue Engineering, Biomaterials, 17, 115-124, 1996.
28. Boyden, S., The Chemotactic Effect of Mixtures of Antibody and Antigen on Polymorphonuclear Leucocytes, J. Exp. Med., 115, 453-466, 1962.
29. Harvath, L., Falk, W., Leonard, E. J., Rapid Quantitation of Neutrophil Chemotaxis—Use of A Polyvinylpyrrolidone-Free Polycarbonate Membrane in A Multiwell Assembly, J. Immunol. Methods, 37, 39-45, 1980.
30. Falk, W., Goodwin, R. H., Leonard, E. J., A 48-Well Micro Chemotaxis Assembly for Rapid and Accurate Measurement of Leukocyte Migration, J. Immunol. Methods, 33, 239-247, 1980.
31. Yao, J., Harvath, L., Gilbert, D. L., Colton, C. A., Chemotaxis by A Cns Macrophage, the Microglia, J. Neurosci. Res., 27, 36-42, 1990.
32. Roth, S. J., Carr, M. W., Rose, S. S., Springer, T. A., Characterization of Transendothelial Chemotaxis of T Lymphocytes, J. Immunol. Methods, 188, 97-116, 1995.
33. Klemke, R. L., Leng, J., Molander, R., Brooks, P. C., Vuori, K., Cheresh, D. A., CAS/Crk Coupling Serves As a "Molecular Switch" for Induction of Cell Migration, Journal of Cell Biology, 140, 961-972, 1998.
34. Ding, Z., Xiong, K, Issekutz, T. B., Chemokines Stimulate Human T Lymphocyte Transendothelial Migration to Utilize VLA-4 in Addition to LFA-1, J. Leukoc. Biol., 69, 458-466, 2001.

35. Jones, D. A., Abbassi, O., McIntire, L. V., McEver. R. P., Smith, C. W., P-Selectin Mediates Neutrophil Rolling on Histamine-Stimulated Endothelial Cells, Biophys. J., 65, 1560-1569, 1993.
36. Brown, D. and Larson, R., Improvements to Parallel Plate Flow Chambers to Reduce Reagent and Cellular Requirements, BMC Immunology, 2, 9-16, 2001.
37. Cinamon, G. and Alon, R., A Real Time in Vitro Assay for Studying Leukocyte Transendothelial Migration Under Physiological Flow Conditions, J. Immunol. Methods, 273, 53-62, 2003.
38. Renard, M., Heutte, F., Boutherin-Falson, O., Finet, M., Boisseau, M. R., Induced Changes of Leukocyte Slow Rolling in an in Flow Pharmacological Model of Adhesion to Endothelial Cells, Biorheology, 40, 173-178, 2003.
39. Munn, L. L., Melder, R. J., Jain, R. K., Analysis of Cell Flux in the Parallel-Plate Flow Chamber—Implications for Cell Capture Studies, Biophys. J., 67, 889-895, 1994.
40. Ley, K., The Selectins As Rolling Receptors. In: The selectins: initiators of leukocyte endothelial adhesion, Vestweber, D, ed. Harwood Academic Publishers, Australia, 63-104, 1997.
41. Papadaki, M. and McIntire, L. V., Quantitative Measurement of Shear-Stress Effects on Endothelial Cells. In: Tissue engineering methods and protocols, Morgan, J. R. and Yarmush, M. L, eds. Humana Press, Totowa, N.J., 577-593, 1999.
42. Ramos, C. L. and Lawrence, M. B., Quantitative Measurement of Cell-Cell Adhesion Under Flow Conditions, In: Tissue engineering methods and protocols, Morgan, J. R. and Yarmush, M. L., eds. Humana Press, Totowa, N.J., 507-519, 1999.
43. Hammer, D. A. and Brunk, D. K., Measuring Receptor-Mediated Cell Adhesion Under Flow: Cell-Free Systems. In: Tissue engineering methods and protocols, Morgan, J. R. and Yarmush, M. L., eds. Humana Press, Totowa, N.J., 543-552, 1999.
44. Jain, R. K., Munn, L. L., Fukumura, D., Melder, R. J., In Vitro and In Vivo Quantification of Adhesion Between Leukocytes and Vascular Endothelium. In: Tissue engineering methods and protocols, Morgan, J. R. and Yarmush, M. L., eds. Humana Press, Totowa, N.J., 553-575, 1999.
45. Li, C. Y., Shan, S., Huang, Q., Braun, R. D., Lanzen, J., Hu, K., Lin, P., Dewhirst, M. W., Initial Stages of Tumor Cell-Induced Angiogenesis: Evaluation Via Skin Window Chambers in Rodent Models, J Natl Cancer Inst, 92, 143-7, 2000.
46. Jain, R. K., Munn, L. L., Fukumura, D., Dissecting Tumour Pathophysiology Using Intravital Microscopy. Nat Rev Cancer, 2, 266-76, 2002.
47. Jain, R. K., Munn, L. L., Fukumura, D., Dissecting Tumour Pathophysiology Using Intravital Microscopy. Nature Reviews Cancer, 2, 266-276, 2002.
48. Jain, R. K., Angiogenesis and Lymphangiogenesis in Tumors: Insights From Intravital Microscopy, Cold Spring Harb.Symp.Quant.Biol., 67, 239-248, 2002.
49. Folkman, J., Bach, M., Rowe, J. W., Davidoff, F., Lambert, P., Hirsch, C., Goldberg, A., Hiatt, H. H., Glass, J., Henshaw, E., Tumor Angiogenesis—Therapeutic Implications, N. Engl. J. Med., 285, 1182-1186, 1971.
50. Weidner, N., Semple, J. P., Welch, W. R., Folkman, J., Tumor Angiogenesis and Metastasis—Correlation in Invasive Breast-Carcinoma, N. Engl. J. Med., 324, 1-8, 1991.
51. Lin, P., Buxton, J. A., Acheson, A, Radziejewski, C, Maisonpierre, P. C., Yancopoulos, G. D., Channon, K. M., Hale, L. P., Dewhirst, M. W., George, S. E., Peters, K. G., Antiangiogenic Gene Therapy Targeting the Endothelium-Specific Receptor Tyrosine Kinase Tie2, Proc. Natl. Acad Sci USA, 95, 8829-34, 1998.
52. Lin, P., Polverini, P., Dewhirst, M., Shan, S., Rao, P. S., Peters, K., Inhibition of Tumor Angiogenesis Using a Soluble Receptor Establishes a Role for Tie2, in Pathologic Vascular Growth, J Clin Invest, 100, 2072-8, 1997.
53. Lin, P., Sankar, S., Shan, S., Dewhirst, M. W., Polverini, P. J., Quinn, T. Q., Peters, K. G., Inhibition of Tumor Growth by Targeting Tumor Endothelium Using a Soluble Vascular Endothelial Growth Factor Receptor, Cell Growth Differ, 9, 49-58, 1998.
54. Heidemann, J., Ogawa, H., Dwinell, M. B., Rafiee, P., Maaser, C., Gockel, H. R., Otterson, M. F., Ota, D. M., Lugering, N., Domschke, W., Binion, D. G., Angiogenic Effects of Interleukin 8 (CXCL8) in Human Intestinal Microvascular Endothelial Cells Are Mediated by CXCR2, J. Biol. Chem., 278, 8508-8515, 2003.
55. Li, Y., Tondravi, M., Liu, J., Smith, E., Haudenschild, C. C., Kaczmarek, M., Zhan, X., Cortactin Potentiates Bone Metastasis of Breast Cancer Cells, Cancer Res, 61, 6906-11, 2001.
56. Higgs, H. N. and Pollard, T. D., Regulation of Actin Filament Network Formation Through Arp2/3 Complex: Activation by a Diverse Array of Proteins, Annu. Rev. Biochem., 70,649-676, 2001.
57. Li, F. Y., Zhang, L., Metzger, R. M., On the Growth of Highly Ordered Pores in Anodized Aluminum Oxide, Chem. Mater., 10, 2470-2480, 1998.
58. Li, A. P., Muller, F., Birner, A., Nielsch, K., Gosele, U., Hexagonal Pore Arrays With a 50-420 Nm Interpore Distance Formed by Self-Organization in Anodic Alumina, J. Appl. Phys., 84, 6023-6026, 1998.
59. Black, C. T., Guarini, K. W., Milkove, K. R., Baker, S. M., Russell, T. P., Tuominen, M. T., Integration of Self-Assembled Diblock Copolymers for Semiconductor Capacitor Fabrication, Appl.Phys.Lett., 79, 409-411, 2001.
60. Black, C. T. and Guarini, K. W., Diblock Copolymers: Self-Assembly for Applications in Microelectronics, In: Encyclopedia of Materials:Science and Technology, Buschow, K H J, ed. Elsevier, New York, 1-6, 2002.
61. Guarini, K. W., Black, C. T., Zhang, Y., Kim, H., Sikorski, E. M., Babich, I. V., Process Integration of Self-Assembled Polymer Templates into Silicon Nanofabrication, Journal of Vacuum Science & Technology B, 20, 2788-2792, 2002.
62. MartinezZaguilan, R., Seftor, E. A., Seftor, R. E. B., Chu, Y. W., Gillies, R. J., Hendrix, M. J. C., Acidic PH Enhances the Invasive Behavior of Human Melanoma Cells, Clinical & Experimental Metastasis, 14, 176-186, 1996.
63. Gillies, R. J., Raghunand, N., Karczmar, G. S., Bhujwalla, Z. M., MRI of the Tumor Microenvironment, J.Magn.Reson.Inaging, 16, 430-450, 2002.
64. Bhujwalla, Z. M., Artemov, D., Ballesteros, P., Cerdan, S., Gillies, R. J., Solaiyappan, M, Combined Vascular and Extracellular PH Imaging of Solid Tumors, NMR Biomed., 15, 114-119, 2002.
65. Helmlinger, G., Schell, A., Dellian, M., Forbes, N. S., Jain, R. K., Acid Production in Glycolysis-Impaired Tumors Provides New Insights into Tumor Metabolism, Clin.Cancer Res., 8, 1284-1291, 2002.

What is claimed is:

1. A bioreactor comprising:
   i. a first substrate having a first surface and an opposite second surface, defining a chamber therebetween the first surface and the opposite second surface of the first substrate for receiving biological cells and a liquid medium;
   ii. an inlet port formed in the first substrate and apart from the chamber;
   iii. a first connection channel formed in the first substrate, wherein the first connection channel is in fluid communication with the inlet port and the chamber for allowing a stream of substance to be delivered to the chamber;
   iv. an outlet port formed in the first substrate and apart from the chamber;
   v. a second connection channel formed in the first substrate, wherein the second connection channel is in fluid communication with the outlet port and the chamber for allowing a stream of substance to be removed from the chamber; and
   vi. confining means positioned in the chamber to form a confinement region to confine the biological cells therein with the liquid medium,
   wherein the chamber, the inlet portion, the first connection channel, the outlet port, and the second connection channel are all formed in the first substrate;
   wherein the confining means comprises a first filter and a second filter, wherein the first filter is positioned proximate to the first connection channel and the second filter is positioned proximate to the second connection channel, and the first filter and the second filter are substantially parallel to each other; and
   wherein each of the first filter and the second filter comprises an array of posts spaced apart from each other not to allow biological cells to pass through it.

2. The bioreactor of claim 1, wherein the first substrate is fabricated from glass, Mylar, PDMS, silicon, a polymer, a semiconductor, or any combination of them.

3. The bioreactor of claim 1, further comprising a second substrate having a first surface and an opposite, second surface, wherein the second substrate is sized such that when the first surface of the second substrate is received by the second surface of the first substrate, the chamber is covered.

4. The bioreactor of claim 3, further comprising at least one supporting member positioned outside the confined region of the chamber for supporting the second substrate.

5. The bioreactor of claim 3, further comprising at least one supporting member positioned inside the confined region of the chamber for supporting the second substrate.

6. A bioreactor comprising:
   i. a first substrate having a first surface and an opposite second surface, defining a chamber therebetween the first surface and the opposite second surface of the first substrate for receiving biological cells and a liquid medium;
   ii. an inlet port formed in the first substrate and apart from the chamber;
   iii. a first connection channel formed in the first substrate, wherein the first connection channel is in fluid communication with the inlet port and the chamber for allowing a stream of substance to be delivered to the chamber;
   iv. an outlet port formed in the first substrate and apart from the chamber;
   v. a second connection channel formed in the first substrate, wherein the second connection channel is in fluid communication with the outlet port and the chamber for allowing a stream of substance to be removed from the chamber; and
   vi. confining means positioned in the chamber to form a confinement region to confine the biological cells therein with the liquid medium, wherein the confining means comprises an array of posts,
   wherein the chamber, the inlet portion, the first connection channel, the outlet port, and the second connection channel are all formed in the first substrate such that, in operation, the stream of substance flows from the inlet port through the first connection channel, the chamber and the second connection channel to the outlet port in a direction that is substantially parallel to the plane of the first surface of the first substrate; and wherein the first substrate further defines a first alternate port and a third connection channel in fluid communication with the first alternate port and the confined region of the chamber for allowing seed biological cells to perfuse only inside the confined region in the chamber.

7. The bioreactor of claim 6, wherein the first substrate is fabricated from glass, Mylar, PDMS, silicon, a polymer, a semiconductor, or any combination of them.

8. The bioreactor of claim 6, further comprising a second substrate having a first surface and an opposite, second surface, wherein the second substrate is sized such that when the first surface of the second substrate is received by the second surface of the first substrate, the chamber is covered.

9. The bioreactor of claim 8, further comprising at least one supporting member positioned outside the confined region of the chamber for supporting the second substrate.

10. The bioreactor of claim 8, further comprising at least one supporting member positioned inside the confined region of the chamber for supporting the second substrate.

11. The bioreactor of claim 6, wherein the stream of substance is controlled so as to provide a gradient to the channel.

12. The bioreactor of claim 6, wherein the stream of substance comprises chemokine.

13. The bioreactor of claim 6, wherein the stream of substance comprises a substance affecting the growth of biological cells.

14. The bioreactor of claim 6, wherein sidewalls at the intersections of the first connection channel with the chamber and the second connection channel with the chamber are tapered to form an angle of inclination between about 10 and 45 degrees from vertical and an enclosed angle between about 30 and 80 degrees.

* * * * *

UNITED STATES PATENT AND TRADEMARK OFFICE
CERTIFICATE OF CORRECTION

PATENT NO.      : 7,534,601 B2
APPLICATION NO. : 10/525559
DATED           : May 19, 2009
INVENTOR(S)     : John P. Wikswo et al.

It is certified that error appears in the above-identified patent and that said Letters Patent is hereby corrected as shown below:

Col. 1, lines 9-11;

"The United States Government may have certain rights to the invention pursuant to these grants." Please delete "may have" and insert --has--.

Signed and Sealed this

Thirtieth Day of June, 2009

JOHN DOLL
*Acting Director of the United States Patent and Trademark Office*